(12) United States Patent
Kelso et al.

(10) Patent No.: US 8,148,071 B2
(45) Date of Patent: Apr. 3, 2012

(54) METHODS AND COMPOSITIONS FOR ISOLATING NUCLEIC ACID

(75) Inventors: David M. Kelso, Wilmette, IL (US);
Sujit Jangam, Chicago, IL (US);
Douglas Yamada, Los Angeles, CA (US); Sally McFall, Evanston, IL (US)

(73) Assignee: Northwestern University, Evanston, IL (US)

( * ) Notice: Subject to any disclaimer, the term of this patent is extended or adjusted under 35 U.S.C. 154(b) by 195 days.

(21) Appl. No.: 12/570,542

(22) Filed: Sep. 30, 2009

(65) Prior Publication Data
US 2010/0092979 A1 Apr. 15, 2010

Related U.S. Application Data

(60) Provisional application No. 61/101,236, filed on Sep. 30, 2008.

(51) Int. Cl.
*C12Q 1/68* (2006.01)
*C07H 21/00* (2006.01)

(52) U.S. Cl. ........................................ 435/6.1; 536/25.4
(58) Field of Classification Search ............... 435/6, 6.1; 536/25.4
See application file for complete search history.

(56) References Cited

U.S. PATENT DOCUMENTS

| | | | | |
|---|---|---|---|---|
| 6,140,047 | A * | 10/2000 | Duff et al. | 435/6 |
| 6,881,537 | B1 * | 4/2005 | Goudsmit et al. | 435/5 |
| 2002/0150907 | A1 * | 10/2002 | Fomovskaia et al. | 435/6 |
| 2008/0113356 | A1 | 5/2008 | Sasaki et al. | |
| 2008/0113357 | A1 | 5/2008 | Baggio et al. | |
| 2008/0166703 | A1 * | 7/2008 | Himmelreich et al. | 435/6 |
| 2010/0055735 | A1 * | 3/2010 | Low et al. | 435/39 |

FOREIGN PATENT DOCUMENTS
EP 1529840 A1 5/2005

OTHER PUBLICATIONS de Kok et al., Use of Real-Time PCR to compare DNA isolation methods. Clinical Chemistry 44 (10) : 2201(1998).*
Jangam et al., Rapid, Point-of-Care Extraction of Human Immunodeficiency Virus Type 1 Proviral DNA from Whole Blood for Detection by Real-Time PCR. J. of Clinical Microbiology 47 (8) : 2363 (2009).*
Jangam et al. "Rapid, Point-of-Care Extraction of Human Immunodeficiency Virus Type 1 Proviral DNA From Whole Blood for Detection by Real-Time PCR," J. Clinical Microbiology, (Jun. 3, 2009) vol. 47,L pp. 2364-2365.

* cited by examiner

*Primary Examiner* — Ethan Whisenant
(74) *Attorney, Agent, or Firm* — Judy M. Mohr; King & Spalding LLP

(57) ABSTRACT

The present invention relates to compositions and methods for isolating and purifying nucleic acid. In particular, the present invention relates to methods of isolating nucleic acid from cells for use in further analysis.

27 Claims, 27 Drawing Sheets

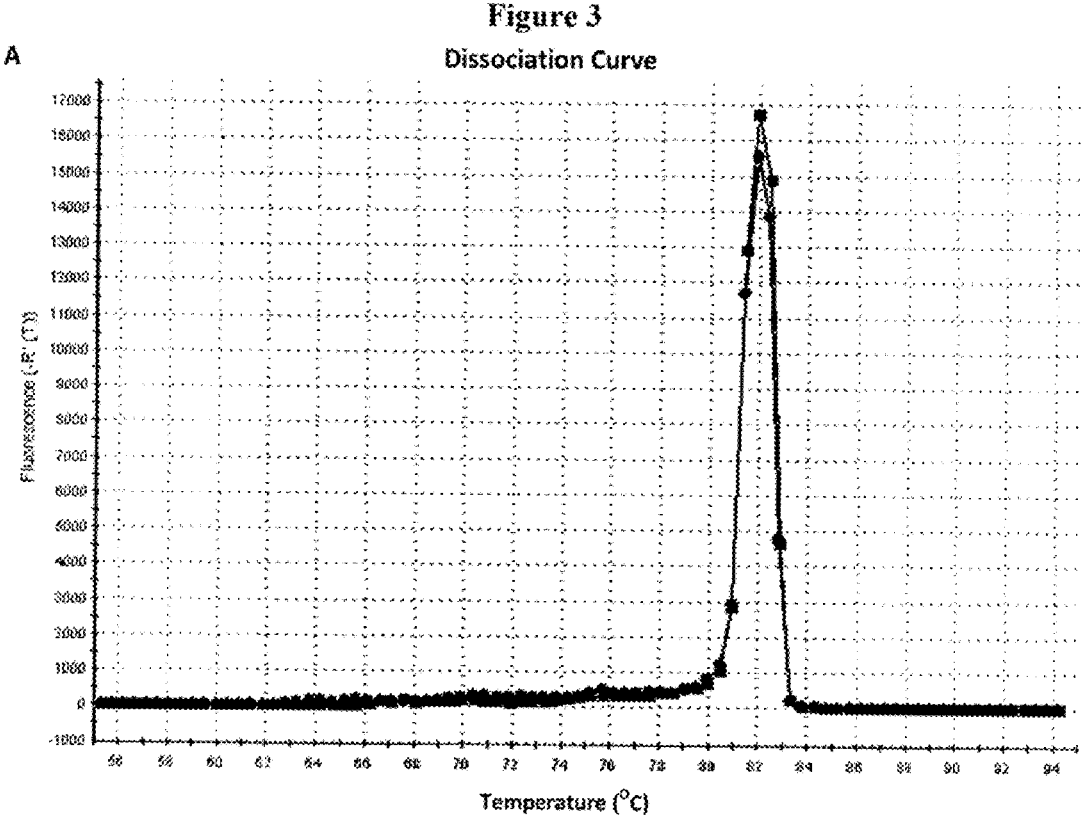
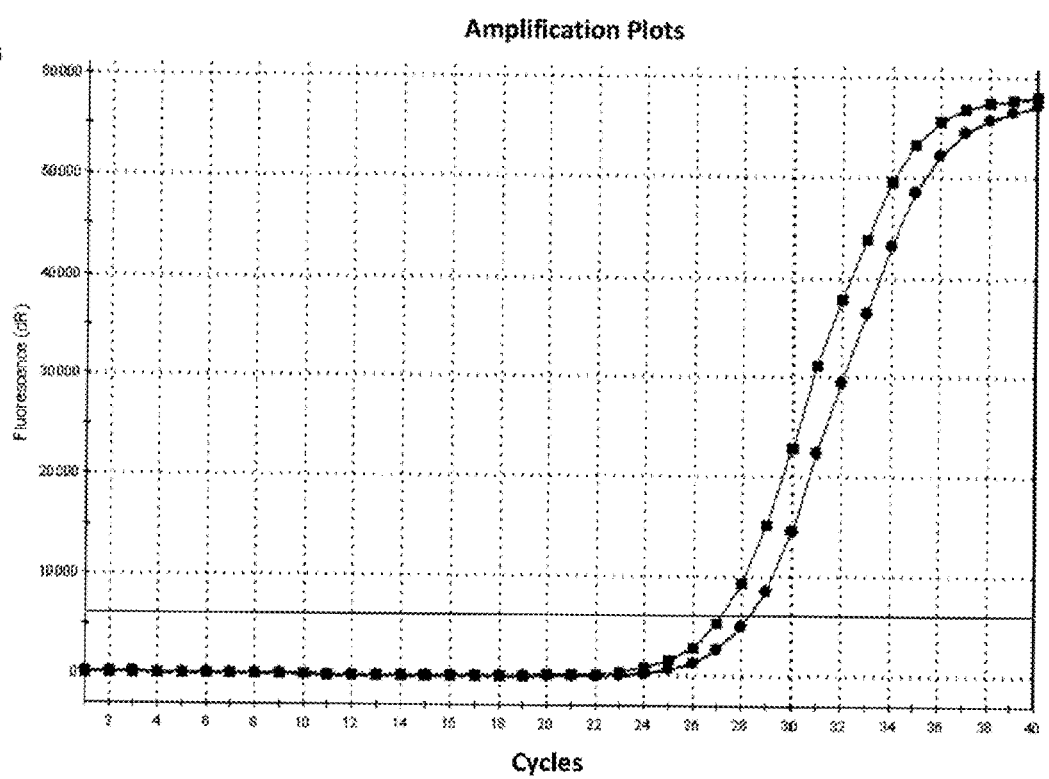
Figure 3

Figure 4
A   Amplification Plots
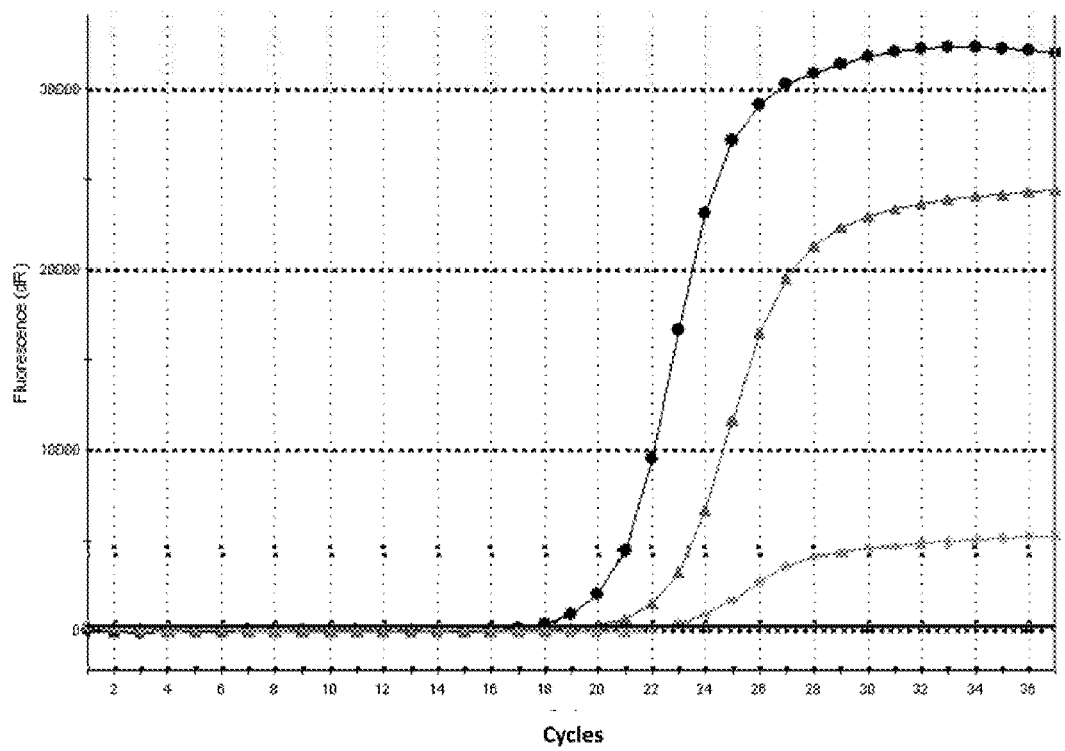
B
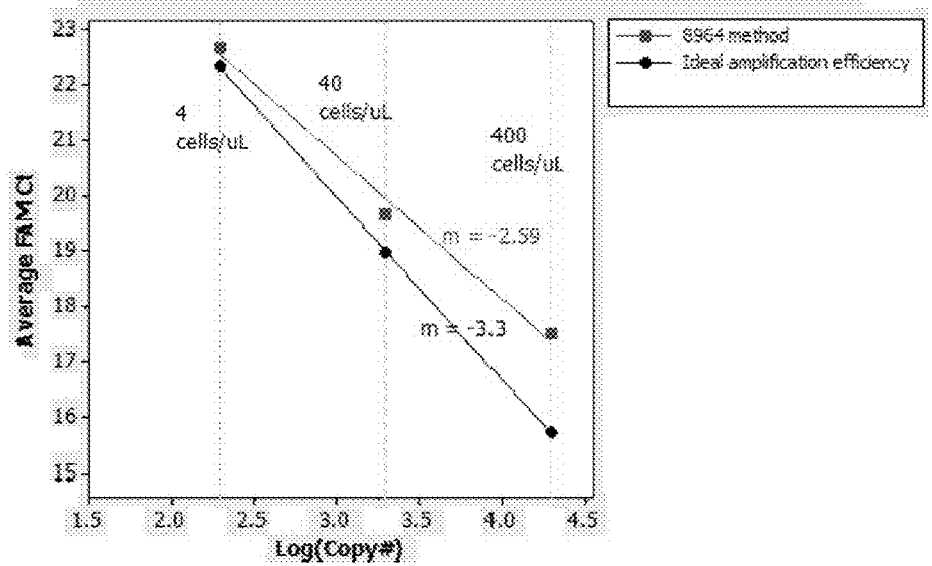

Figure 5 (CONT)
B
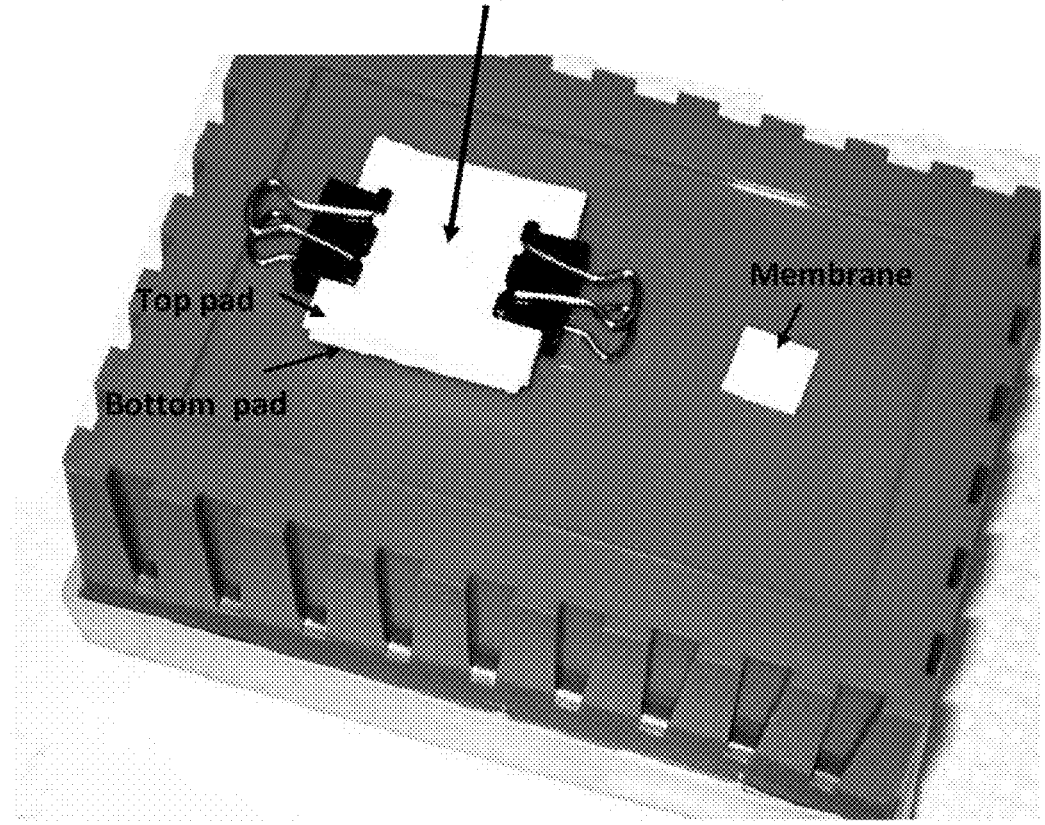
C
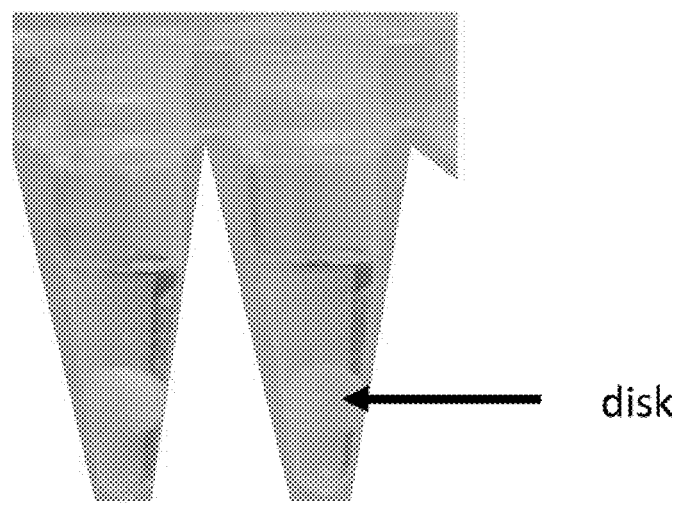

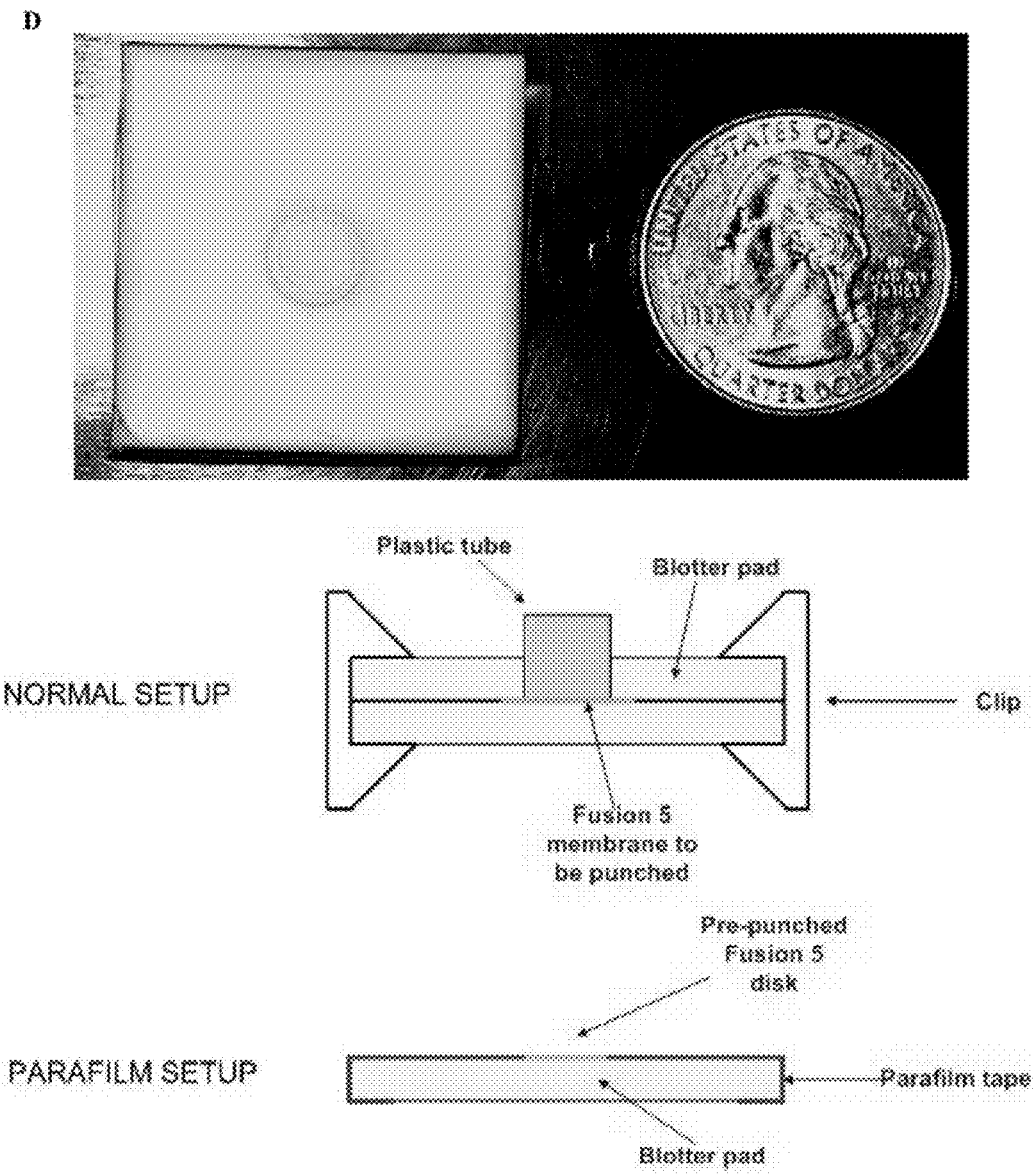

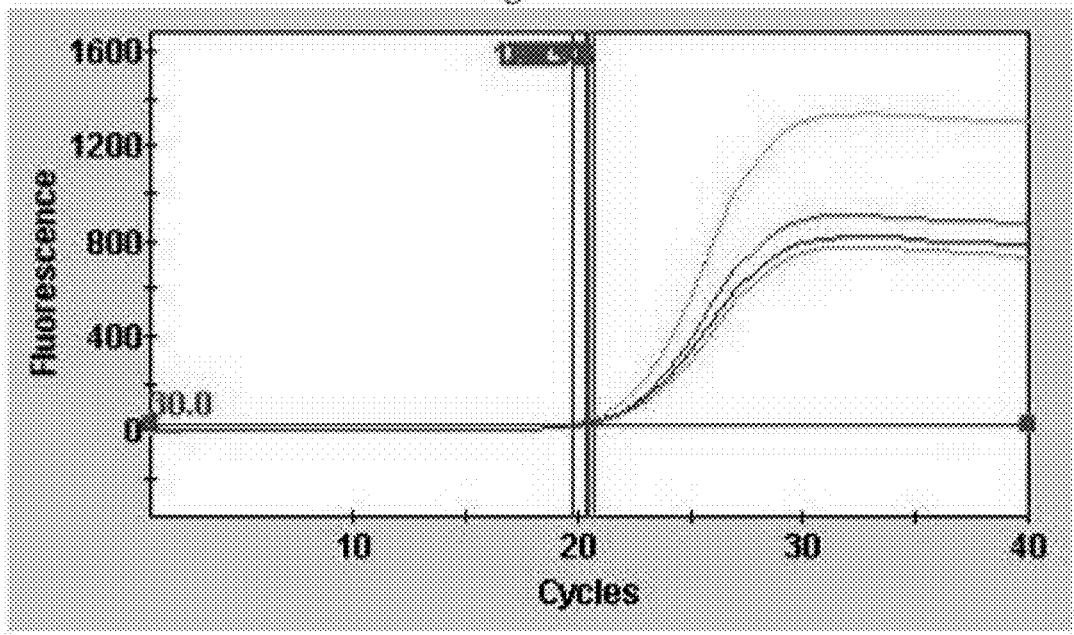
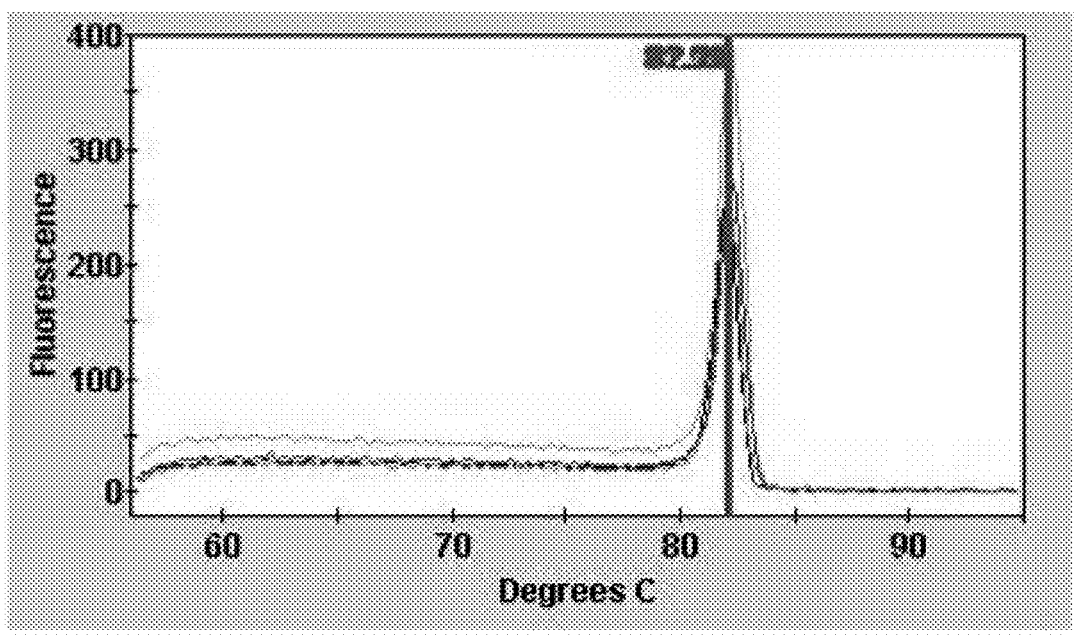
Figure 6

FIGURE 7
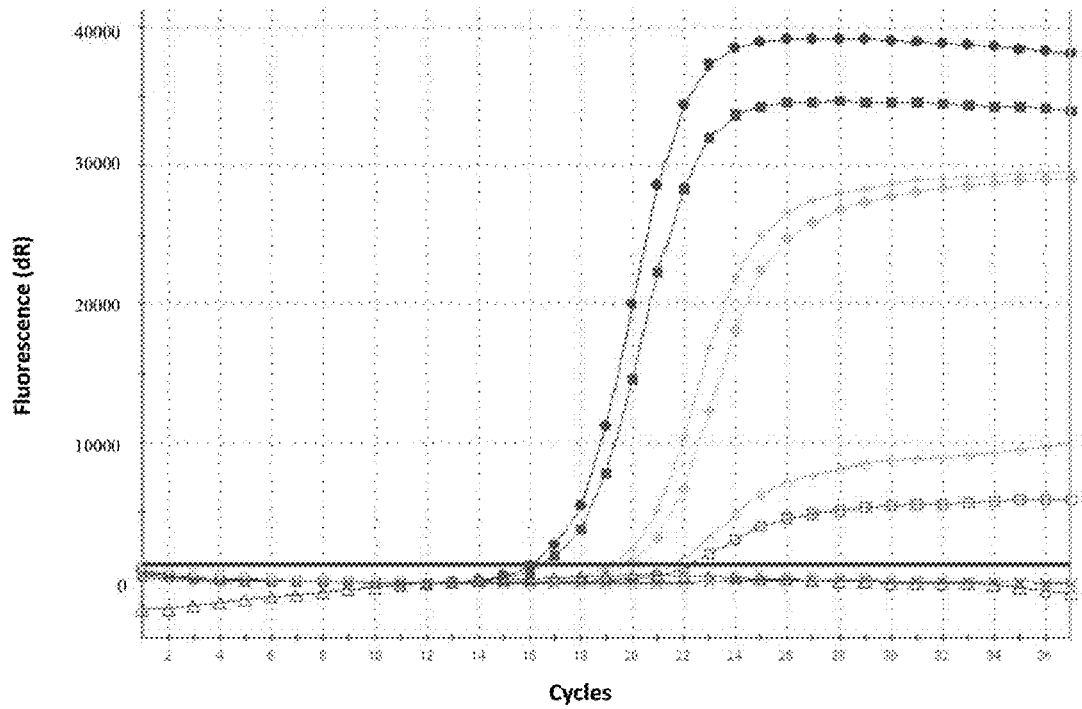
A
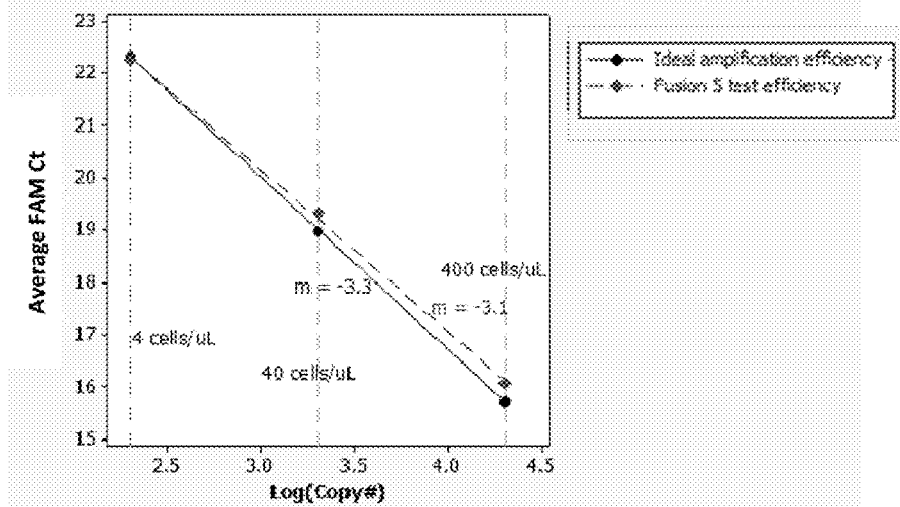
B

Figure 10
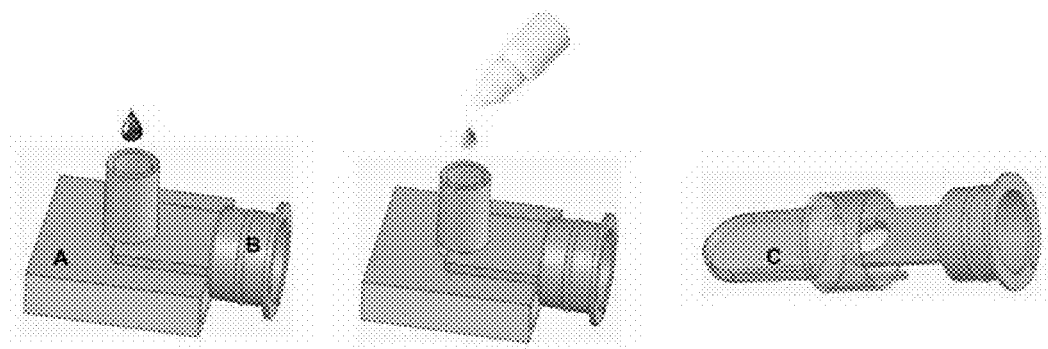
Step 1: Collect blood sample and filter cells
Step 2: Add wash buffer
Step 3: Insert membrane holder (B) into cuvette (C) and seal
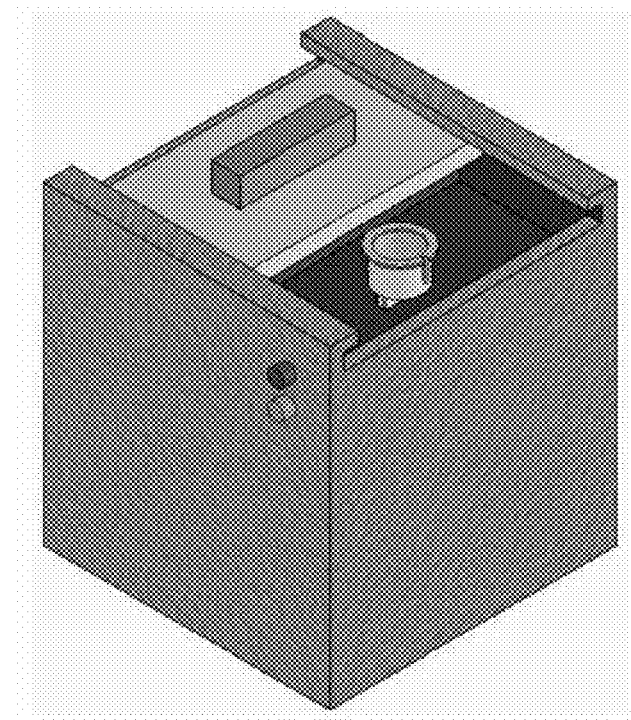
Step 4: Insert cuvette into real-time thermal cycler and close shutter to initiate processing Standard Curve Log Fit Values FAM Standards, RSq:0.995
FAM, Y = -3.138*LOG(X) + 28.58, Eff. = 108.3%

Amplification Plots

Figure 17
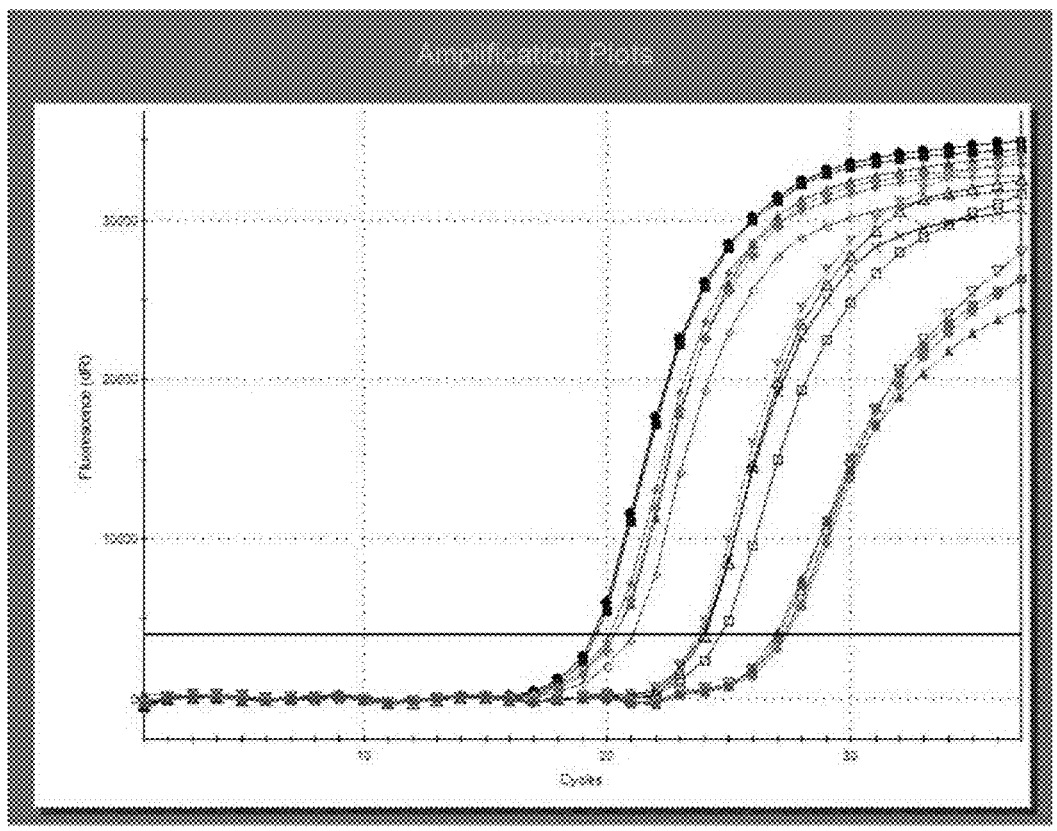
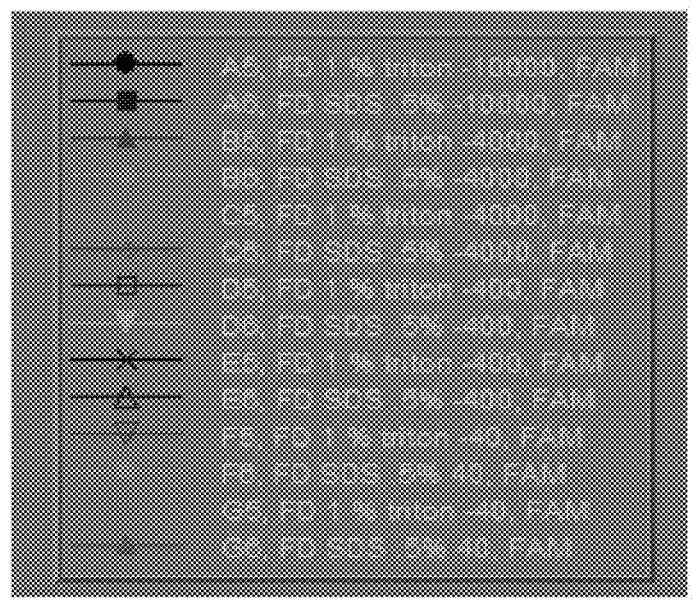

Amplification Plots

Cell or Nucleic acid separation membrane

Energy directors could be molded into the part to facilitate sonic welding of membrane to plastic Extended Neck Blood entry port Blotter material Thumb press tab to release handle after processing Handle Spring fixture to hold blotter in intimate contact with separation membrane

METHODS AND COMPOSITIONS FOR ISOLATING NUCLEIC ACID

CROSS REFERENCE TO RELATED APPLICATIONS

This application claims priority to U.S. Provisional Application Ser. No. 61/101,236, filed: Sep. 30, 2008, which is herein incorporated by reference in its entirety.

FIELD OF THE INVENTION

The present invention relates to compositions and methods for isolating and purifying nucleic acid. In particular, the present invention relates to methods of isolating nucleic acid from cells for use in further analysis.

BACKGROUND OF THE INVENTION

It is estimated that up to 5% of infants born to HIV seropositive mothers are HIV infected due to mother-to-child-transmission (MTCT). In 2005 alone, about 2.3 million infants were infected with HIV and about 2 million of these were in sub-Saharan Africa. Mortality rates are very high in infants infected with HIV. In HIV infected infants, mortality rate is as high as 26-45% by the first year of birth and 35-59% by the second, stressing the urgent need for early and accurate diagnosis and therapy. Early diagnosis of HIV could result in timely treatment of HIV infected infants and may result in lower mortality rates.

HIV DNA PCR detects close to 100% of all infections at 6-weeks of age. Roche AMPLICOR® HIV-1 DNA test version 1.5 is the most widely used commercial DNA PCR assay that is capable of detecting all subtypes of HIV and has been used for diagnosis of HIV in infants. Nucleic Acid Sequence Based Amplification (NASBA) has been shown to be as sensitive and specific as DNA PCR. Recently, dried blood spots (DBS) based DNA PCR has been developed for early diagnosis of HIV in infants. It does not involve venipuncture and only requires a sterile lancet for a heel prick. Briefly, a blood sample is collected on 903 filter paper (Whatman Inc., Kent, UK) and dried. Blood can be stored and transported easily in the form of DBS. Furthermore, it has been demonstrated that there is a 100% correlation between diagnosis from heel prick blood and venous blood by DNA PCR. Many groups have reported successful PCR with high sensitivity and specificity from DNA extracted from DBS. DBS have resulted in improved accessibility to rural areas. A DBS sample is collected from infants at the POC when they are brought in for their first immunization at the age of 6 weeks. The samples are shipped to a central laboratory for testing and the results are then shipped back to the rural clinic in time for the second immunization at 10 weeks post-birth.

However, very often, the results do not get back in time for the second immunization resulting in high lost-to-lab and lost to follow-up rates up to 50%. Furthermore, the extraction of DNA in a central lab requires expensive equipment and trained personnel making the test inaccessible to developing nations due to cost at about 50 USD/test. In contrast, results from early POC testing can be provided to the infant's caregiver at the same appointment, and appropriate treatment can be initiated significantly reducing lost-to-follow up rates.

Many challenges must be overcome when conducting HIV DNA tests both in centralized laboratories and out in the field. Large laboratories use automated or semi-automated robotic systems for high-volume HIV viral load assays. However, sample processing is typically the most troublesome part of these tests. Currently, sample-processing procedures involve many steps, often requiring centrifugation and extraction steps. Also, these methods often do not adequately purify the target nucleic acid. They often leave inhibitory or interfering substances in the reaction mixture that can cause inhibition of the amplification reaction and result in false-negative results. The manual nature of current sample-processing techniques also can lead to specimen cross-contamination, which can cause false-positive results.

Considerable effort has been made in trying to automate the sample preparation process, since this would allow for the more widespread use of PCR or other nucleic analysis techniques. However, existing automated high-throughput systems perform multiple extraction and purification steps, and still require certain manual preparations, including sample and reagent loading, and waste removal. Hence, highly trained technicians are required to conduct the assay and maintain the instrument. The automated systems are very expensive because they use complex robotic arms to move solutions or magnetic particles and precision instruments to pipette liquids. The cost of an automated system is often difficult to justify for smaller laboratories, especially those in resource limited settings. Cross-contamination is also a problem since they employ amplification technologies. Clinical laboratories often use separate rooms for reagent preparation, sample preparation, amplification, and post-amplification analysis. For these reasons, despite the automation, DNA proviral testing is considered high-complexity tests under the Clinical Laboratory Improvement Amendments (CLIA). To date, no Nucleic Acid Test (NAT) system has qualified for CLIA-waived status, largely because of the difficulties in automating sample preparation and reagent handling.

Performing field-use or near-patient NATs involves even more challenges, especially since they will inevitably be conducted by less-experienced users in non-laboratory environments.

What is needed are fast, inexpensive, and efficient methods of preparing samples for nucleic acid analysis.

SUMMARY OF THE INVENTION

The present invention relates to compositions and methods for isolating and purifying nucleic acid. In particular, the present invention relates to methods of isolating nucleic acid from cells for use in further analysis.

For example, in some embodiments, the present invention provides a biological sample processing kit, comprising: at least one sample processing device comprising a sample collection membrane with a pore size configured to retain nucleic acid (e.g., in white blood cells or white blood cell nuclei) and allow lysed red blood cells to flow through; and a buffer configured to lyse red blood cells retained on said membrane. In some embodiments, the kit further comprises reagents for performing a nucleic acid (e.g., genomic DNA or pathogen) detection reaction. In some embodiments, the nucleic acid detection reaction is an amplification reaction (e.g., including but not limited to, polymerase chain reaction (e.g., real time PCR), loop mediated isothermal amplification, ligase chain reaction, rolling circle replication, nucleic acid sequence based amplification and self-sustained sequence replication). In some embodiments, the membrane holds up to 200 µl or more (e.g., greater than 1 µl, 5 µl, 10 µl, 50 µl, greater than 100 µl, 50 µl-200 µl, 100 µl-200 µl, or 150 µl-200 µl) of blood. In some embodiments, the membrane has a length of less than 10 cm (e.g., less than 5 cm, 3 cm, 1, etc.) and a width of less than 3 cm (e.g., less than 2 cm, 1 c, 0.5 cm, 0.3 cm, etc.). In some embodiments, the sample processing device further comprises a blotter material in physical contact with the membrane. In some embodiments, the physical contact permits horizontal lateral or vertical flow of fluid from said membrane to said blotter. In some embodiments, the kit further comprises reagents for detecting amplified nucleic acid. In some embodiments, the amplified nucleic acid is pathogen (e.g., viral) nucleic acid. In some embodiments, the kit further comprises reagents for lysing white (e.g., comprising the nucleic acid of interest) and red blood cells.

In some embodiments, the present invention provides a system, comprising at least one sample processing device comprising a sample collection membrane with a pore size configured to retain nucleic acid (e.g., in white blood cells or white blood cell nuclei) and allow lysed red blood cells to flow through; and a buffer configured to lyse red blood cells retained on said membrane. In some embodiments, the system further comprises a detection apparatus. In some embodiments, the detection apparatus is configured to directly receive the membrane (e.g., in a membrane holder). In some embodiments, the detection apparatus is an apparatus for performing an amplification reaction (e.g., polymerase chain reaction (e.g., real time PCR), loop mediated isothermal amplification, ligase chain reaction, rolling circle replication, nucleic acid sequence based amplification and self-sustained sequence replication.

In further embodiments, the present invention provides method of processing biological samples, comprising: contacting at least one sample processing device comprising a sample collection membrane with a pore size configured to retain nucleic acid (e.g., in white blood cells or white blood cell nuclei) and allow red blood cell components to flow through with a blood sample; and contacting the membrane with a buffer under conditions such that the buffer lyses red blood cells, removes debris, and leaves purified white blood cells or components thereof on the membrane. In some embodiments, the method is a multiplex method (e.g., uses multiple membranes simultaneously). In some embodiments, the method further comprises the step of performing a nucleic acid (e.g., genomic DNA or pathogen nucleic acid) detection reaction on the purified white blood cells. In some embodiments, the nucleic acid detection reaction is an amplification reaction (e.g., including but not limited to, polymerase chain reaction (e.g., real time PCR), loop mediated isothermal amplification, ligase chain reaction, rolling circle replication, nucleic acid sequence based amplification and self-sustained sequence replication). In some embodiments, the method purifies up to 200 μl of blood. In some embodiments, the method further comprises the step of detecting the amplified nucleic acid. In some embodiments, the amplified nucleic acid is pathogen (e.g., viral) nucleic acid. In some embodiments, the method further comprises the step of lysing white (e.g., containing nucleic acid) and red blood cells prior to contacting the sample with the sample processing device.

DESCRIPTION OF THE FIGURES

FIG. 3A shows melt curves of specific product formation when $\beta_2$-microglobulin was tested from whole blood using SYBR green detection. FIG. 3B shows amplification curves of PCR in combination with 8964 procedure to detect $\beta_2$-microglobulin from whole blood using SYBR green detection.

FIG. 4A shows amplification plots indicating that up to 4 cells/μL can be detected using the 8964 procedure in conjunction with the Abbott RealTime® HIV-1 assay. FIG. 4B shows standard curves indicating that PCR efficiency is slightly below 100%.

FIG. 6A shows amplification curves indicating that PCR in combination with Fusion 5 procedure can be used for detection of $\beta_2$-microglobulin from whole blood using SYBR green detection. FIG. 6B shows melt curves that show specific product formation of $\beta_2$-microglobulin from whole blood using SYBR green detection.

FIG. 7A shows amplification plots indicating that up to 4 cells/μL can be detected using the Fusion 5 procedure in conjunction with an Abbott RealTime® HIV-1 assay. FIG. 7B shows standard curves indicating that PCR efficiency is very close to 100%.

FIG. 10 shows an exemplary device of the present invention.

FIG. 17 shows blood samples containing HIV-1 (10,000-40 copies) lysed by adding to a microtube containing a pellet of freeze dried lysing reagent and tested for HIV-1 using real-time PCR.

DEFINITIONS

Figure 1:
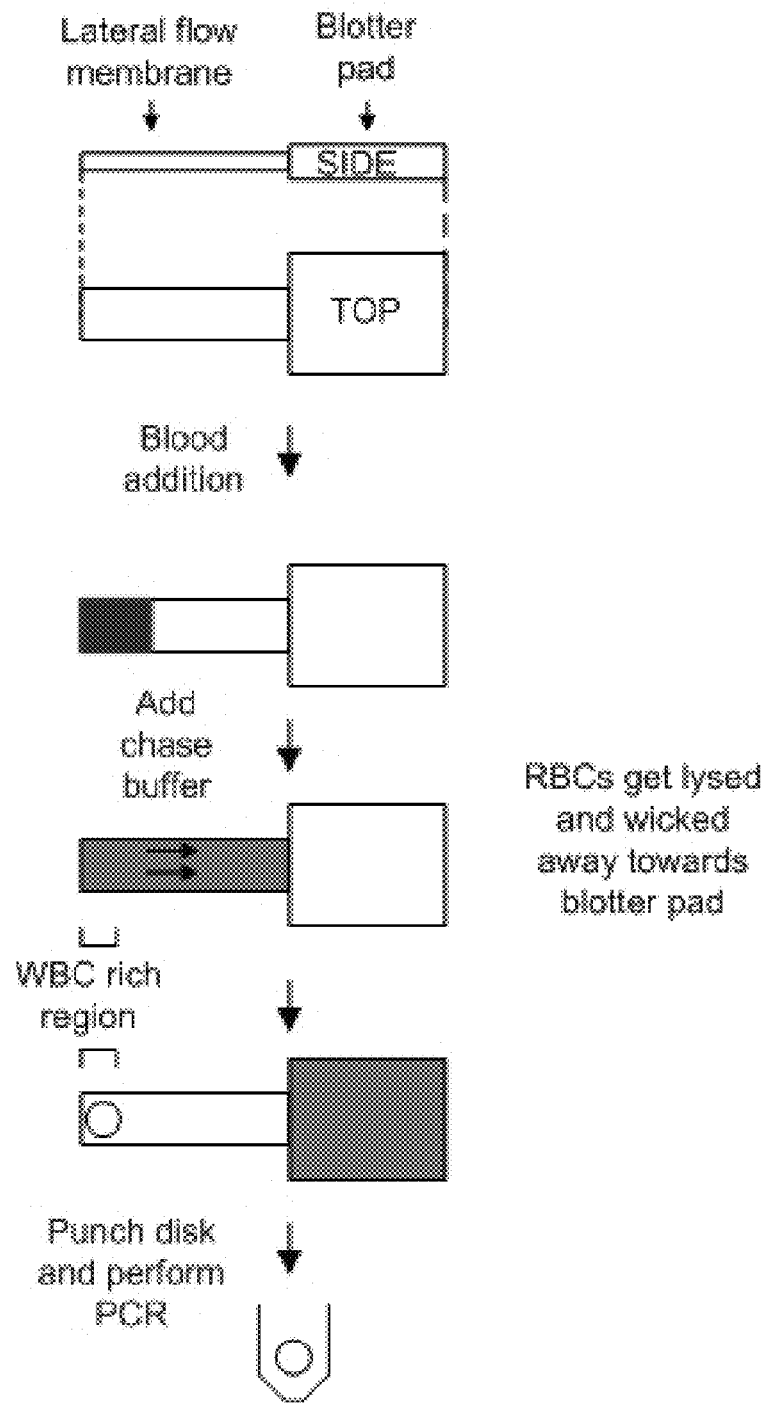
FIG. 1 shows a schematic of a lateral flow technique for cell separation.

To facilitate an understanding of this disclosure, terms are defined below:

"Purified polypeptide" or "purified protein" or "purified nucleic acid" means a polypeptide or nucleic acid of interest or fragment thereof which is essentially free of, e.g., contains less than about 50%, preferably less than about 70%, and more preferably less than about 90%, cellular components with which the polypeptide or polynucleotide of interest is naturally associated.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Purified product" refers to a preparation of the product which has been isolated from the cellular constituents that the product is normally associated and from other types of cells which may be present in the sample of interest.

A "capture reagent," as used herein, refers to an unlabeled specific binding member that is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips, are all suitable examples. It is contemplated and within the scope of the present invention that the solid phase also can comprise any suitable porous material.

As used herein, the terms "detect", "detecting", or "detection" may describe either the general act of discovering or discerning or the specific observation of a detectably labeled composition.

The term "polynucleotide" refers to a polymer of ribonucleic acid (RNA), deoxyribonucleic acid (DNA), modified RNA or DNA, or RNA or DNA mimetics. This term, therefore, includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "nucleic acid amplification reagents" includes conventional reagents employed in amplification reactions and includes, but is not limited to, one or more enzymes having polymerase activity, enzyme cofactors (such as magnesium or nicotinamide adenine dinucleotide (NAD)), salts, buffers, deoxynucleotide triphosphates (dNTPs; for example, deoxyadenosine triphosphate, deoxyguanosine triphosphate, deoxycytidine triphosphate and deoxythymidine triphosphate) and other reagents that modulate the activity of the polymerase enzyme or the specificity of the primers.

As used herein, the terms "complementary" or "complementarity" are used in reference to polynucleotides (i.e., a sequence of nucleotides such as an oligonucleotide or a target nucleic acid) related by the base-pairing rules. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of identity. There may be partial homology or complete homology. A partially identical sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids.

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% \ G+C)$, when a nucleic acid is in aqueous solution at 1 M NaCl (see e.g., Anderson and Young, Quantitative Filter Hybridization, in Nucleic Acid Hybridization (1985). Other references include more sophisticated computations which take structural as well as sequence characteristics into account for the calculation of Tm.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably at least 5 nucleotides, more preferably at least about 10-15 nucleotides and more preferably at least about 15 to 30 nucleotides, or longer. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

DETAILED DESCRIPTION OF THE INVENTION

The present invention relates to compositions and methods for isolating and purifying nucleic acids. In particular, the present invention relates to methods of isolating nucleic acids from human cells for use in further analysis.

Cell separation using filtration membranes has been studied in great detail. Nucleic acid isolation using lysing agents on membranes has been successfully performed as well. However, most such methods require a pressure drop in the form of a syringe-type system and/or require multiple washes to get rid of contaminating proteins and other cellular components. Some methods also require a digestion step involving proteinase K digestion. There are reagents that are available that enable PCR from whole blood. However, these reagents can only process small volumes of blood that do not generate sufficient nucleic acids for amplification reactions involving low copy number targets such as viral nucleic acids. There are devices that can collect blood and separate cellular components but do not clean them enough for PCR.

Experiments conducted during the course of development of embodiments of the present invention resulted in the development of a method that enables the usage of up to 200 μL (e.g., from approximately 1 μl to greater than 100 μl) whole blood and also enables real-time optical detection. Many methods also require agitation in order to separate contaminants. The methods of embodiments of the present invention do not require a pressure drop for operation and can use, for example, only a one chase step with RBC lysis buffer to isolate the WBCs from other contaminating components of blood, eliminating the need for agitation as well.

An exemplary buffer that finds use in the kits, compositions and methods of the present invention is 0.8M $NH_4Cl$, nuclease free $H_2O$ and 10-20 mM NaOH. Good results were obtained with 10 mM NaOH because of improved S/N, although any number of buffers can be used.

Figure 5:
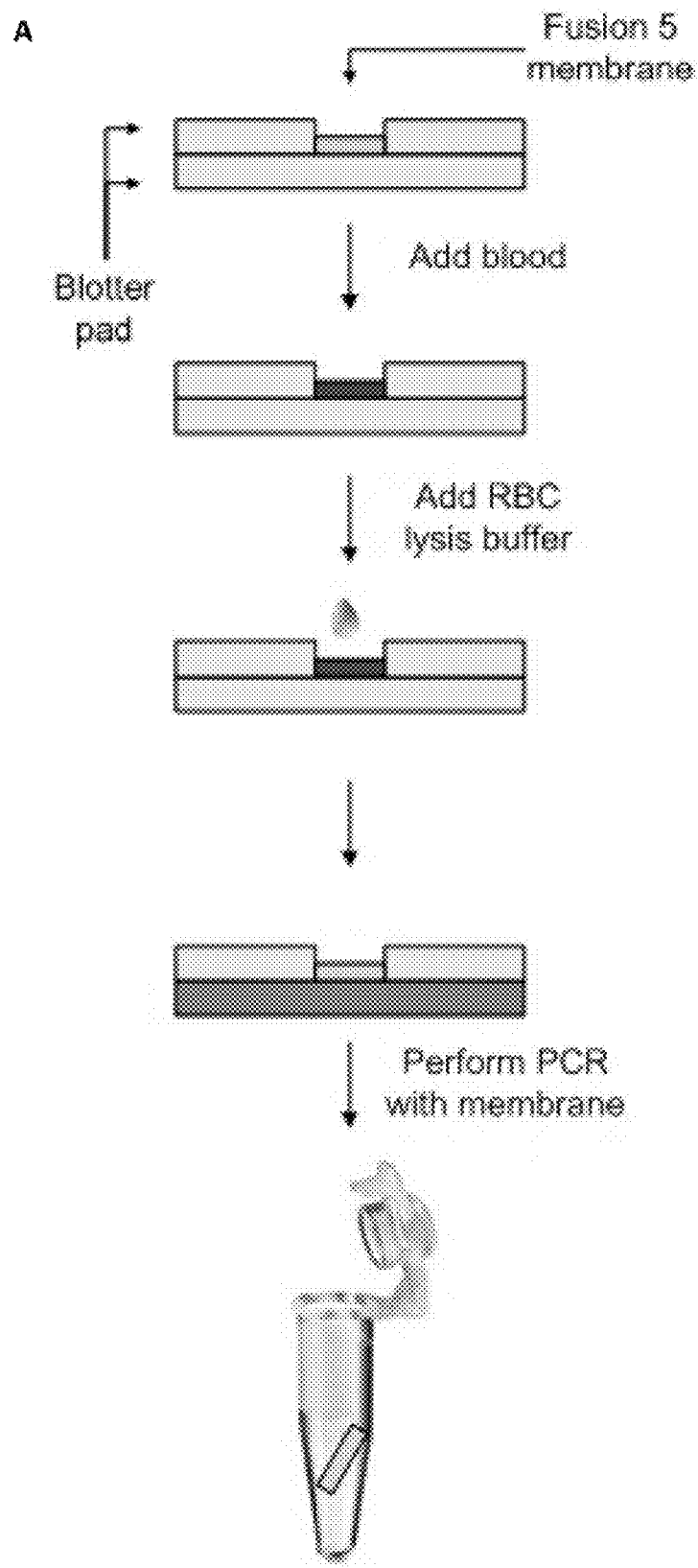
FIG. 5A shows a schematic of the vertical flow technique for cell separation.
FIG. 5B shows a picture of the setup.
FIG. 5C shows a picture of disk in the reaction tube.
FIG. 5D shows a picture of an alternative setup.

In some embodiments, the invention provides a membrane configured to separate blood components. In some embodiments, the cell separation step takes place by capillary action by placing a blotter pad below the membrane while RBC lysis buffer is added on the top (FIG. 5). In other embodiments, the assay is performed using lateral flow, where a blotter pad is placed on the side of the membrane resulting in lateral flow (FIG. 1). The end result is the entrapment of cells on the surface of the membrane which enter PCR or other nucleic acid analysis methods.

I. Devices

As described above, embodiments of the present invention provide devices and systems for performing separation and analysis reactions. In some embodiments, devices comprise a membrane for capturing white blood cells. In some embodiments, the membrane has a pore size of approximately 1 to 50 µM (e.g., 5-20 µM). In some embodiments, methods are lateral flow methods (e.g., as described in FIG. 1). In other embodiments, vertical flow methods are utilized (e.g., as described in FIG. 5). The present invention is not limited to a particular membrane. In some embodiments, the membrane is in contact with blotter paper (e.g., to adsorb waste material). In some embodiments, the membrane has a pore size of approximately 1 to 50 µM (e.g., 5-20 µM). As described in the Experimental section below, a number of membranes were tested and found to be suitable in the methods of embodiments of the present invention.

One exemplary device and method of use is depicted in FIG. 10. In some embodiments, the device has an opening for inserting blood or other fluids. In some embodiments (Step 1 of FIG. 10), the filtration module contains a cell separation membrane and an absorbent pad that separates the leukocytes. In some embodiments, blood is added to the module that results in separation of cellular components from the plasma by capillary action.

In some embodiments, the next step (Step 2 of FIG. 10) is a wash step with 500-1000 µL wash buffer to separate the erythrocytes, platelets and other blood components from the leukocytes. In some embodiments, the whole procedure takes about 2-3 min.

In some embodiments (Step 3 of FIG. 10), the membrane holder with the disk (with entrapped leukocytes or nucleic acids) is then removed from the module and used as PCR template by inserting into a reaction vessel specifically designed for real-time PCR in the presence of a membrane holder.

In some embodiments (Step 4 of FIG. 10), a real-time PCR instrument that has been adapted to work with the reaction vessel is utilized. The reaction vessel has a large surface to volume ratio to aid in efficient thermal transfer for fast thermal cycling. It also has a polished side wall for fluorescence detection. The circular cap ensures good sealing. The thickness of the sidewall was chosen based on the thickness of the membrane holder so as to allow 1-1.5 mm window for fluorescence detection.

In some embodiments, vertical flow methods utilize a membrane sandwiched between two pieces of blotter paper. In other embodiments, parafilm is used as the top layer instead of blotter paper.

In some embodiments, the method involves the following steps: 1) dispense a volume of whole blood on a filtration membrane/absorbant pad sandwich, 2) rinse membrane with a buffer, 3) transfer the membrane to an analysis solution. This removes RBC cell debris, platelets and serum contaminants without a pressure drop and without further purification of the nucleic acid. The membrane pore size is chosen such that lymphocytes cannot pass through the membrane. This method is also suitable for use on dried blood spots on membranes.

In some embodiments, systems and/or devices of the present invention are shipped containing all components necessary to perform purification and analysis (e.g., amplification reagents). In some embodiments, additional reaction components are supplied in separate vessels packaged together into a kit.

Any of these compositions, alone or in combination with other compositions disclosed herein or well known in the art, may be provided in the form of a kit. Kits may further comprise appropriate controls and/or detection reagents. Any one or more reagents that find use in any of the methods described herein may be provided in the kit.

In some embodiments, systems that automate one or more steps of the process may be used and system employing multiple parallel membranes for higher throughput may be used. For example, a system may comprise automated or multiple sample delivery to a membrane or membranes (e.g., via a multi-pipette or other dispensing device). One or more membranes may be positioned in a sample processing component with the ability to insert, remove, cut, or otherwise process membranes by hand or via robotics or other automated processes. Fluid may be supplied or removed from the system via tubing, channels, or other fluidic components to facilitate sample processing, washing, or other desired functions. In some embodiments, purified samples are transferred manually of in an automated fashion to a reaction chamber or chambers that cause the isolated nucleic acid to be chemical process (e.g., amplified, reverse transcribed, labeled, etc.). In some embodiments, the system comprises detection hardware and/or software to permit detection of the nucleic acid or a label associated with the nucleic acid and/or to process data associated with a detection event or events. The system may be self-contained in a single apparatus or may be provided as two or more separate components.

II. Methods

As described above, the present invention provides sample preparation devices and methods of using the devices. In some embodiments, the present invention provides a quick and simple means of preparing nucleic acid (e.g., genomic DNA) from whole blood for further analysis (e.g., PCR or other amplification method). This method finds use in many different diagnostic and genotyping systems. For example, in experiments conducted during the course of development of embodiments of the present invention, DNA purified using the methods was used for detection of HIV-1 proviral DNA in whole blood using real-time PCR and detection of human genes (β2-microglobulin and β-Globin) with both real-time PCR and LAMP. These experiments demonstrated that the nucleic acid was of sufficient purity (e.g., free from interfering contaminants and inhibitors) and quantity to function with diverse nucleic acid amplification techniques, without further isolation or purification. Additional experiments resulted in the development of a device for implementing such isolation/amplification processes.

The compositions and methods described herein find use in diagnosis of HIV and other diseases at a point-of-care location. The compositions and methods of the present invention further find use as a processing method for dried blood spots. In some embodiments, dried blood spots are collected at a point of care and then mailed to a central lab for further processing.

In some embodiments, the methods and compositions described herein are quantitative and can be used to determine viral reservoirs (e.g., HIV) in infected subjects. In other embodiments, the methods are qualitative and distinguish positive from negative samples.

In further embodiments, the methods and compositions described herein are used for detection of cellular mRNA and in subsequent analyses (e.g., gene expression studies).

In yet other embodiments, the compositions and methods described herein are used as an inexpensive alternative to amplify genomic DNA from cell culture suspensions without having to purify using other extensive protocols. It does not incorporate any pressure drop and hence is free from the requirement of complex filtration modules or centrifuges. The amplified DNA is free in solution and thus can be used for downstream cloning and other applications. In some embodiments, lysing agents are included on the membrane. In some embodiments, cells (e.g., white and red blood cells) are lysed prior to contacting them with the sample preparation devices of embodiments of the present invention. Exemplary lysing methods are described, for example, in Example 2 below.

In still further embodiments, the compositions and methods described herein are used for loop mediated isothermal amplification (LAMP) applications.

A. Sample

Any sample suspected of containing the desired material for purification and/or analysis may be used according to the disclosed methods. In some embodiments, the sample is biological sample. Such a sample may be cells (e.g. cells suspected of being infected with a virus), tissue (e.g., biopsy samples), blood, urine, semen, or a fraction thereof (e.g., plasma, serum, urine supernatant, urine cell pellet or prostate cells), which may be obtained from a patient or other source of biological material, e.g., autopsy sample or forensic material.

B. Modification/Analysis/Detection

The purified sample may be detected using any suitable methods, including, but not limited to, those disclosed herein. The description below provides exemplary techniques for biological molecules such as nucleic acids and proteins. Other techniques may be applied for biological molecules or non-biological molecules, as desired or needed.

Examples of nucleic modification/analysis/detection methods include, but are not limited to, nucleic acid sequencing, nucleic acid hybridization, and nucleic acid amplification. Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing. Illustrative non-limiting examples of nucleic acid hybridization techniques include, but are not limited to, in situ hybridization (ISH), microarray, and Southern or Northern blot. Nucleic acids may be amplified prior to or simultaneously with detection.

Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800, 159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

Non-amplified or amplified target nucleic acids can be detected by any conventional means. For example, target mRNA can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety. In some embodiments, the Abbott RealTime® Assay (See e.g., US 2005/0227257, herein incorporated by reference in its entirety) is utilized.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and many types of interacting label pairs are known (e.g., U.S. Pat. No. 6,534,274, herein incorporated by reference in its entirety).

Another example of a detection probe having self-complementarity is a "molecular beacon" (see U.S. Pat. Nos. 5,925, 517 and 6,150,097, herein incorporated by reference in entirety). Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS).

Other self-hybridizing probes are well known to those of ordinary skill in the art. By way of non-limiting example, probe binding pairs having interacting labels (e.g., see U.S. Pat. No. 5,928,862, herein incorporated by reference in its entirety) may be adapted for use in the compositions and methods disclosed herein. Probe systems used to detect single nucleotide polymorphisms (SNPs) might also be used. Additional detection systems include "molecular switches," (e.g., see U.S. Publ. No. 20050042638, herein incorporated by reference in its entirety). Other probes, such as those comprising intercalating dyes and/or fluorochromes, are also useful for detection of amplification products in the methods disclosed herein (e.g., see U.S. Pat. No. 5,814,447, herein incorporated by reference in its entirety).

In some embodiments, detection methods are qualitative (e.g., presence or absence of a particular nucleic acid). In other embodiments, they are quantitative (e.g., viral load).

C. Data Analysis

In some embodiments, following purification and detection, a computer-based analysis program is used to translate the raw data generated by the detection assay (e.g., the presence, absence, or amount of a given target molecule) into data of predictive value for a clinician or researcher. In some embodiments, the software program is integrated into an automated device. In other embodiments, it is remotely located. The clinician can access the data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

Any method may be used that is capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw data, the prepared format may represent a diagnosis or risk assessment (e.g., HIV infection status) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

EXPERIMENTAL

The following examples are provided to demonstrate and illustrate certain preferred embodiments and aspects of the compositions and methods disclosed herein, but are not to be construed as limiting the scope of the claimed invention.

Example 1

This Example describes two methods of blood collection and purification to separate white blood cells from the other components of blood. The method removes PCR inhibitors and PCR can be directly performed and the sample collection membrane.

Figure 2:
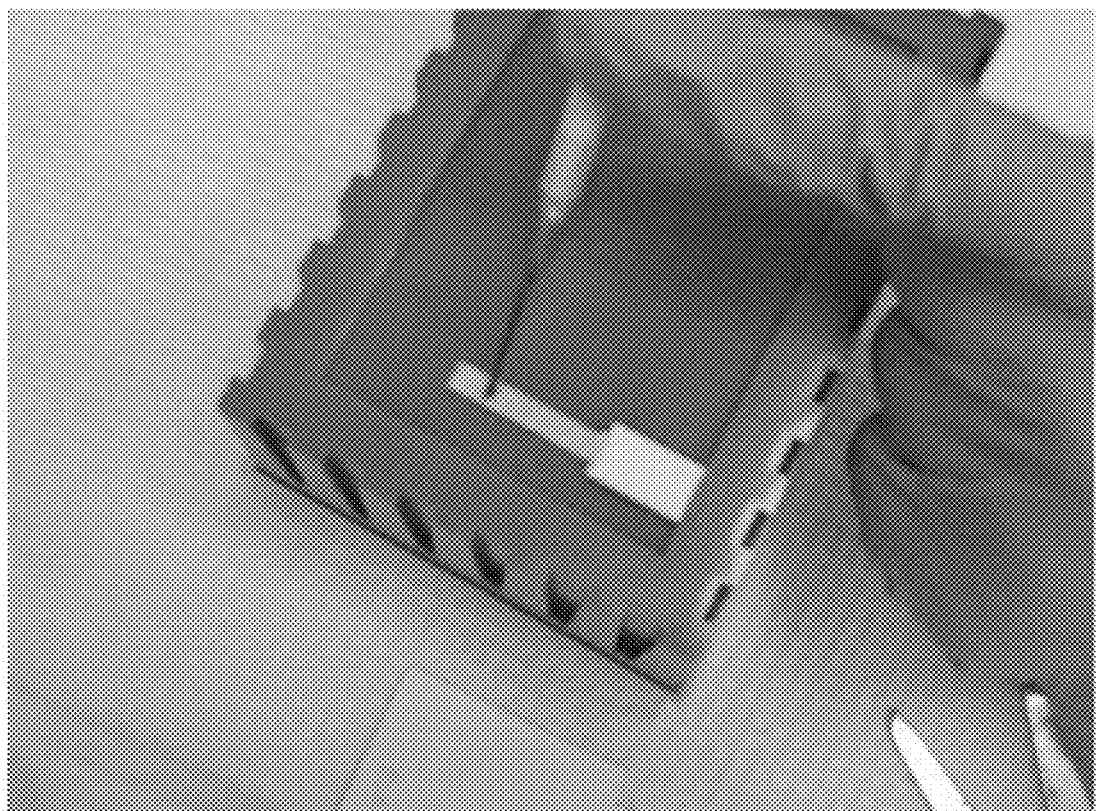
FIG. 2 shows a picture of the setup used in embodiments of the present invention (bottom right). A picture of the tube with the glass fibers broken up after PCR is shown on the bottom left.

Lateral Flow Based Separation:

In this method size-based separation of cells is performed laterally by using a chase buffer as shown in FIGS. 1 and 2.

The chase buffer lyses the RBCs and leaves the genetic material in the WBCs intact. The WBCs get lysed in the subsequent PCR reaction in the presence of detergents and due to thermal cycling. The wicking action of the membrane results in the movement of RBC debris and other proteinaceous material due to the small pore size of the membrane. The movement of the WBCs is impeded by the pore size. Various membranes such as HF90 (Millipore), HF75 (Millipore), HF135 (Millipore), 8964 (Ahlstrom) and AE99 (Whatman) were tried that yielded successful results for detection of genomic DNA from normal blood. Least variability was observed with 8964 glass fibers. This membrane allows the collection of up to 100 µL of blood in a 6 mm disk. The volume of chase buffer required to clear the RBCs and other contaminants was about 0.5-0.7 mL. The total processing time was 4-5 min.

Using the 8964 fibers, β2-microglobulin from human blood was easily detected as shown in FIG. 3a and FIG. 3b. All amplification reactions were done with the following polymerases: Taq, Tth and HemoKlenTaq. Furthermore, HIV proviral DNA was successfully detected from whole blood from an HIV-1 seronegative donor spiked with cultured 8E5 cells that harbor a single copy of the HIV-1 provirus in the range of 4-400 cells/µL (FIG. 4). Another parameter that was evaluated was the slope of the standard curve generated using various dilutions of the 8E5 cells in blood (FIG. 4b). The slope was slightly more than the −3.3 required for 100% efficiency indicating a lower PCR efficiency than 100%. However, 4 cells/µL was reliably detected using this technique.

Vertical Flow Based Separation:

In this method size-based separation of cells is performed vertically by using a chase buffer. The chase buffer specifically lyses the RBCs and leaves the WBCs intact. The wicking action of the membrane results in the movement of RBC debris and other proteinaceous material due to the small pore size of the membrane. The movement of the WBCs is impeded by the pore size. Most of the wicking action is vertical but some lateral flow based separation is also observed. Various membranes such as VF1 (Whatman), VF2 (Whatman), MF1 (Whatman), LF1 (Whatman) and Fusion 5 (Whatman) were tried that yielded successful results for detection of genomic DNA from normal blood via PCR. All amplification reactions were done with the following polymerases: Taq, Tth and HemoKlenTaq. Least variability was observed with Fusion 5 membrane. This membrane allows the collection of up to 200 µL of blood in a 7 mm disk. The volume of chase buffer required to clear the RBCs and other contaminants was about 1 mL. The procedure is a shown in FIG. 5.

The total procedure takes 4-5 min. Using the Fusion 5 membrane, β2-microglobulin from human blood was easily detected as shown in FIG. 6a and FIG. 6b. Furthermore, HIV proviral DNA was successfully detected from whole blood from an HIV-1 seronegative donor spiked with cultured 8E5 cells that harbor a single copy of the HIV-1 provirus in the range of 0.4-400 cells/µL (FIG. 7). Another parameter that was evaluated was the slope of the standard curve generated using various dilutions of the 8E5 cells in blood (FIG. 7b). The slope was very close to the −3.3 required for 100% efficiency indicating PCR efficiency close to 100%. Also LOD measurement indicated that 0.2 cells/µL was reliably detected using this technique.

Figure 8:
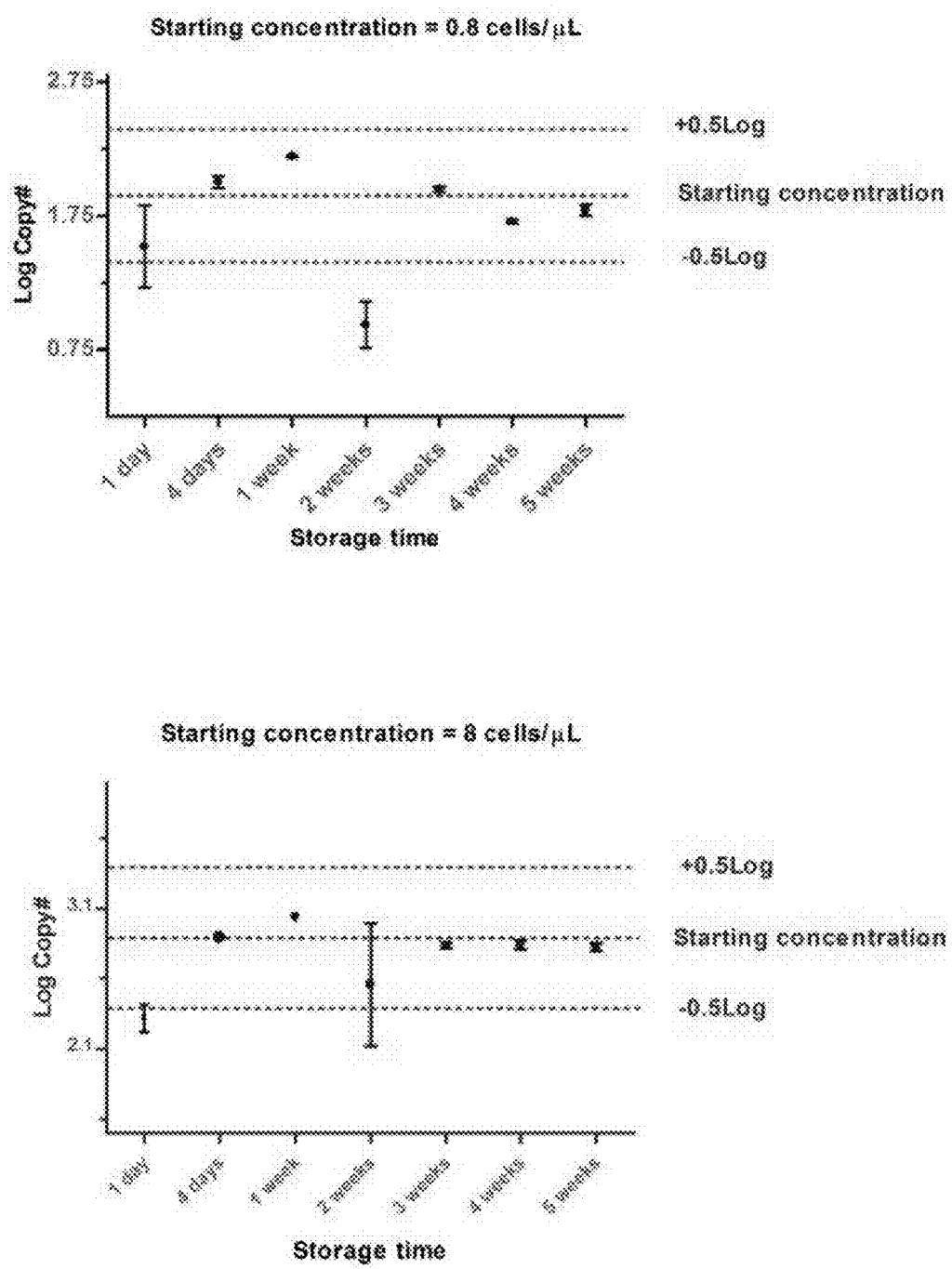
FIG. 8 shows that the number of copies detected did not change significantly after storage for 5 weeks.

The above vertical flow method was also tested after drying blood samples on the membrane for a 0-5 weeks at 37° C. in presence of desiccant and then chasing it with RBC lysis buffer. The results obtained are shown in FIG. 8. FIG. 8 indicated that the number of copies detected did not change significantly even after storage for 5 weeks. Similar results were obtained with blood spots that were chased after blood collection and then dried before PCR. These experiments showed that this method can be used for collection of dried blood spots which can then be mailed to a central lab where the rest of the process is completed.

Figure 9:
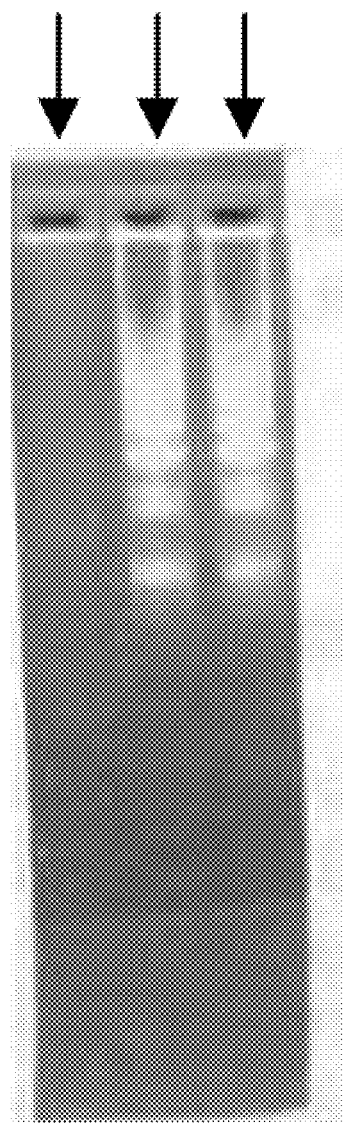
FIG. 9 shows agarose gel electrophoresis showing the formation of ladder pattern expected of LAMP products.

LAMP (loop mediated isothermal amplification) was also successfully performed with the lateral flow method. The data in FIG. 9 show that LAMP was successfully performed to detect β$_2$-microglobulin from blood processed by the lateral flow method. The membrane used was Nitrocellulose AE99 (Whatman).

In addition to the above examples, lysing agents can be immobilized on the surface of the membrane and can be washed away using capillary action. This was demonstrated by using FTA (Whatman) paper. A blotter pad was placed below the FTA paper and the method described above was performed. The data is shown in table 1.

TABLE 1

| Method type | Ct |
|---|---|
| FTA normal | 26.26 |
| FTA normal | 26.11 |
| FTA lateral | 24.67 |
| FTA lateral | 25.75 |

Example 2

Blood Genomic DNA Isolation

This Example describes additional methods for isolation of genomic DNA. In some embodiments, order to increase the amount of genomic DNA isolated from blood, a pre-lysing step was added to the original method. While the additional step improves the yield of nucleic acid, it may or may not be necessary depending on the requirements of the PCR assay and sensitivity required. For applications that require whole cells to be assayed, this step is not needed. Pre-lysing extends the realm of samples to bacterial samples and viral samples where cell size or virion size is too small for effective cell capture. With those sample matrices, pre-lysing will help release nucleic acids that can be captured by the separation membrane. Thus, bacterial and/or viral DNA can be detected. Pre-lysing can also be used with tissue samples such as material obtained from swabs or biopsies that can be pre-lysed and the lysate can then be used for nucleic acid isolation via the following the protocol. Furthermore, by using the appropriate detergent for pre-lysis, nuclei can be captured specifically without releasing nucleic acids. Other modifications include, 1) A larger disk size (9 mm diameter) can be used instead of the 7 mm disk used in the original method to shorten processing time. 2) To minimize interference of disk with the optics of the real-time thermal cycler, an adhesive transfer tape such as the 3M Double-coated polyester diagnostic tape (product#9965) can be used to immobilize the disk on the wall of the reaction tube away from the path of excitation and emission optics.

Figure 11:
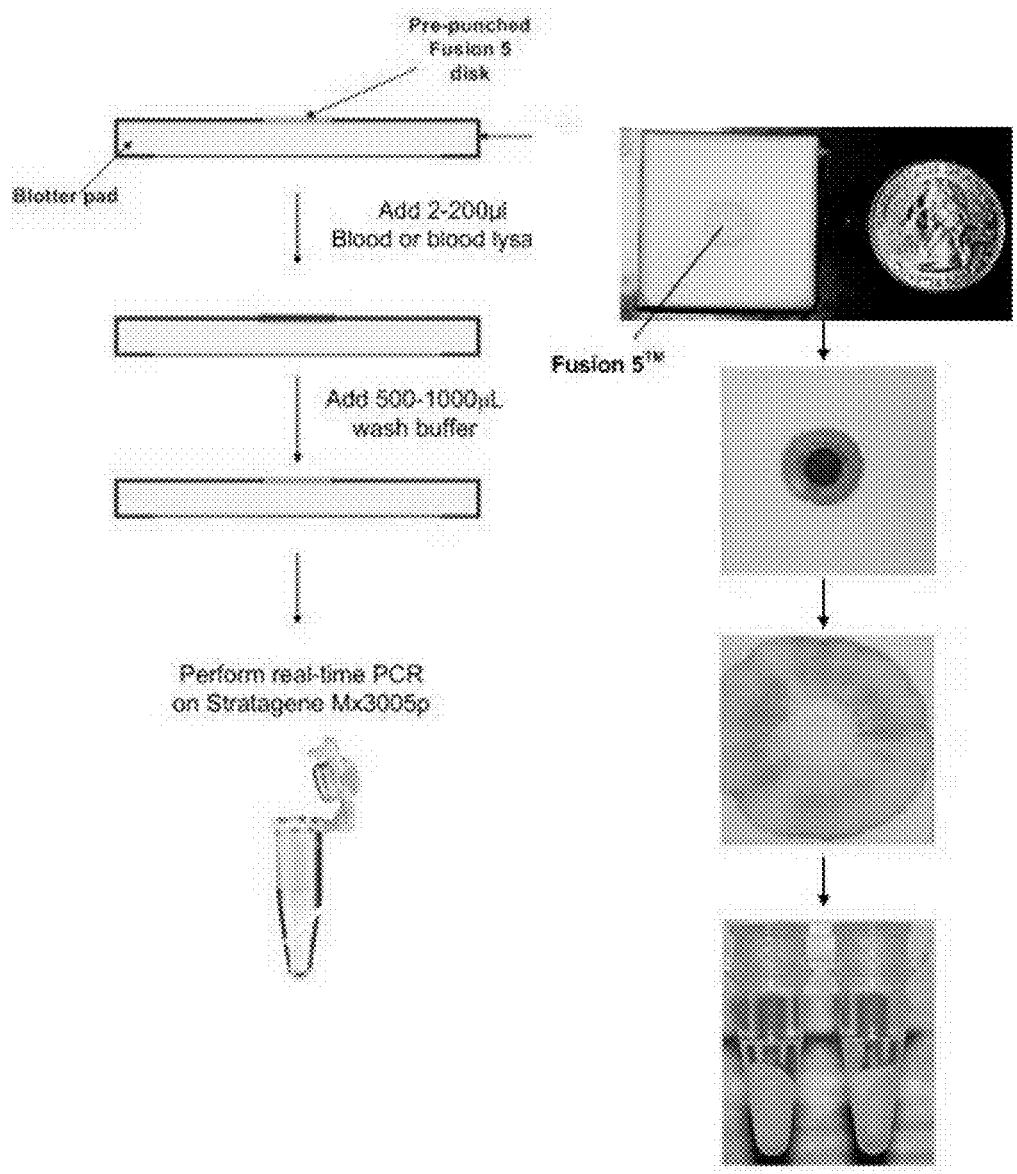
FIG. 11 shows a schematic of an exemplary protocol for rapid isolation of nucleic acids.
Figure 12:
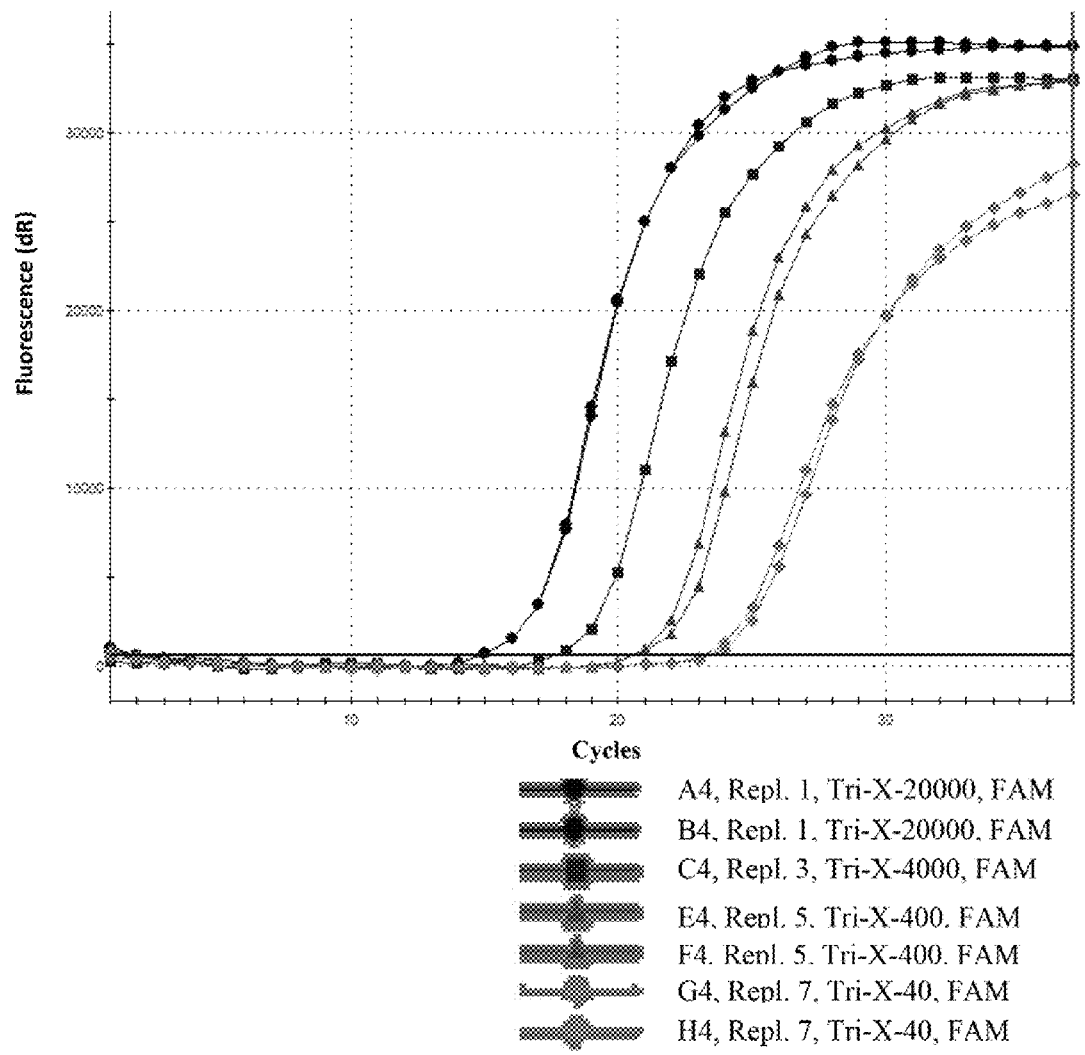
FIG. 12 shows amplification plots obtained with blood reconstituted with 8E5 cells to obtain a total of 20,000-40 HIV-1 copies. HIV-1 DNA is detected in this real-time PCR assay.
Figure 13:
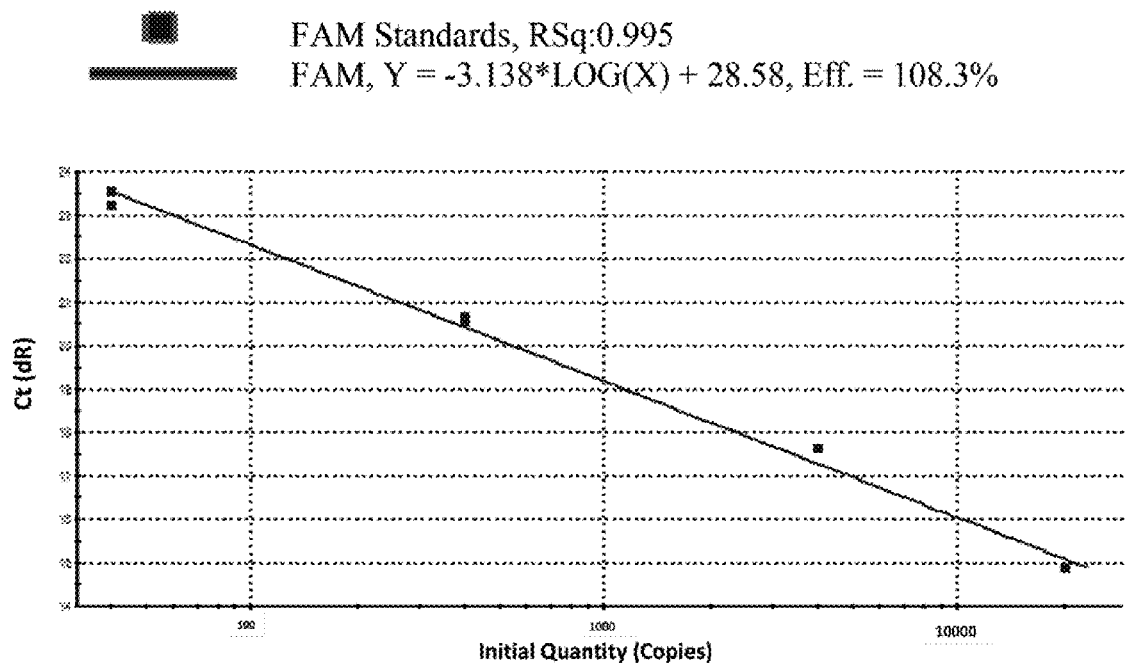
FIG. 13 shows that a standard curve obtained with modified method shows approximately 100% PCR efficiency.
Figure 14:
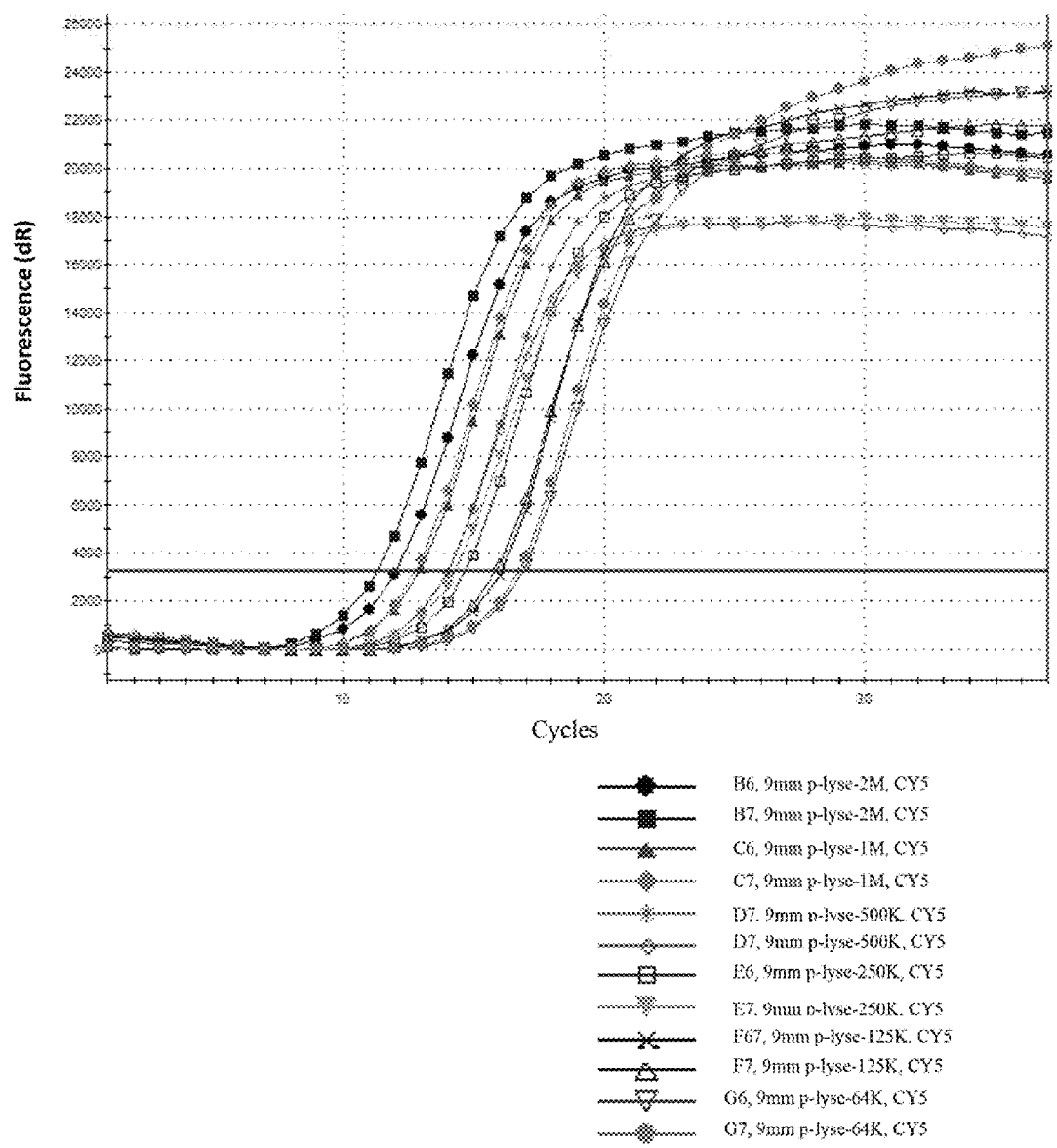
FIG. 14 shows amplification plots obtained with blood containing different total count of White Blood Cells (WBCs) in the range of 62500-20000000 cells.
Figure 15:
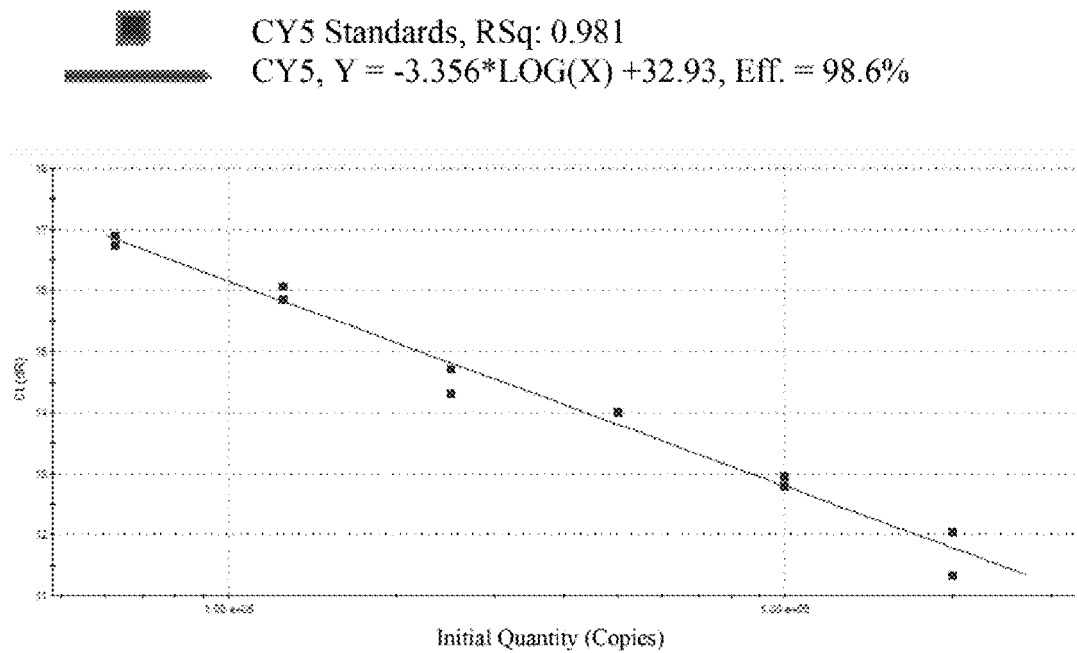
FIG. 15 shows standard curves obtained with blood containing different total count of White Blood Cells (WBCs) in the range of 62500-20000000 cells.

Modified Protocol for Nucleic Acid Isolation:

A schematic of the original process is shown in FIG. 1 and FIG. 5 of the provisional patent application. A schematic of the modified process is shown in FIG. 11.

In the modified method, a blood sample is treated with a lysing agent to lyse all the cellular components of blood including RBCs and WBCs (step 1). This releases genomic DNA in the lysate which is then added to the filtration membrane (step 2) that physically entraps the released genomic DNA. This is followed by adding 600-1000 µl of 10 mM NaOH to the disk that then washes away ghosts and hemoglobin (step 3). The disk containing template genomic DNA is then added to a PCR reaction (step 4). The blood samples used for this study were reconstituted with 8E5 cells that harbor a single copy of HIV-1 DNA to obtain 400-0.4 HIV-1 copies/µl blood. The reconstituted blood sample was then used for nucleic acid isolation. The blood samples are tested for HIV-1 detection and the detection of an endogenous gene namely, human β-globin. A multiplexed real-time PCR assay is used for detection.

Figure 16:
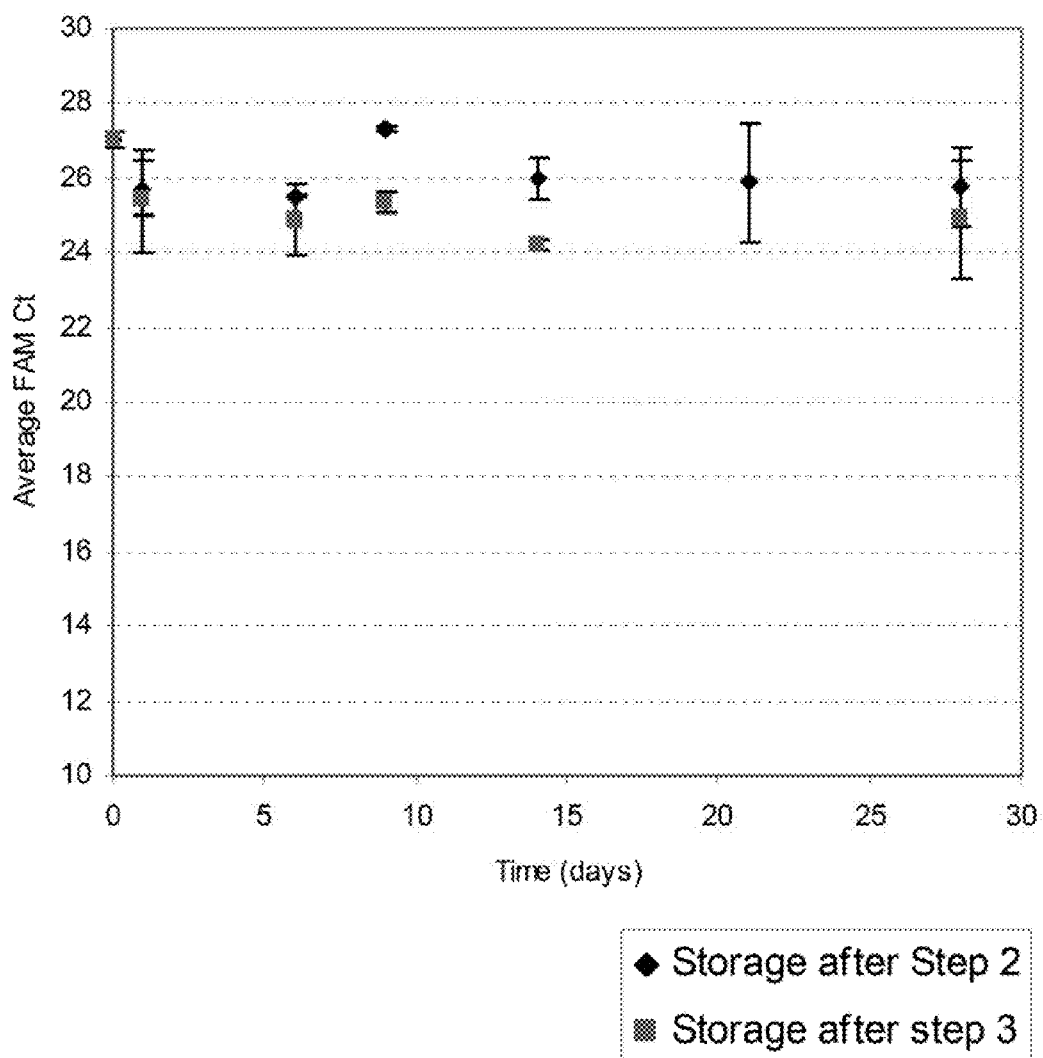
FIG. 16 shows that HIV-1 DNA is stable after storage up to one month. Blood samples used for this study were spiked with 40 copies of HIV-1 (8E5 cells)

Using the modified method as little as 10 copies of HIV-1 can be detected consistently in 100 µl blood. Furthermore, isolated DNA can be stored after step 2 or step 3 for at least 1 month (FIG. 16).

Pre-Lysing Methods

Figure 18:
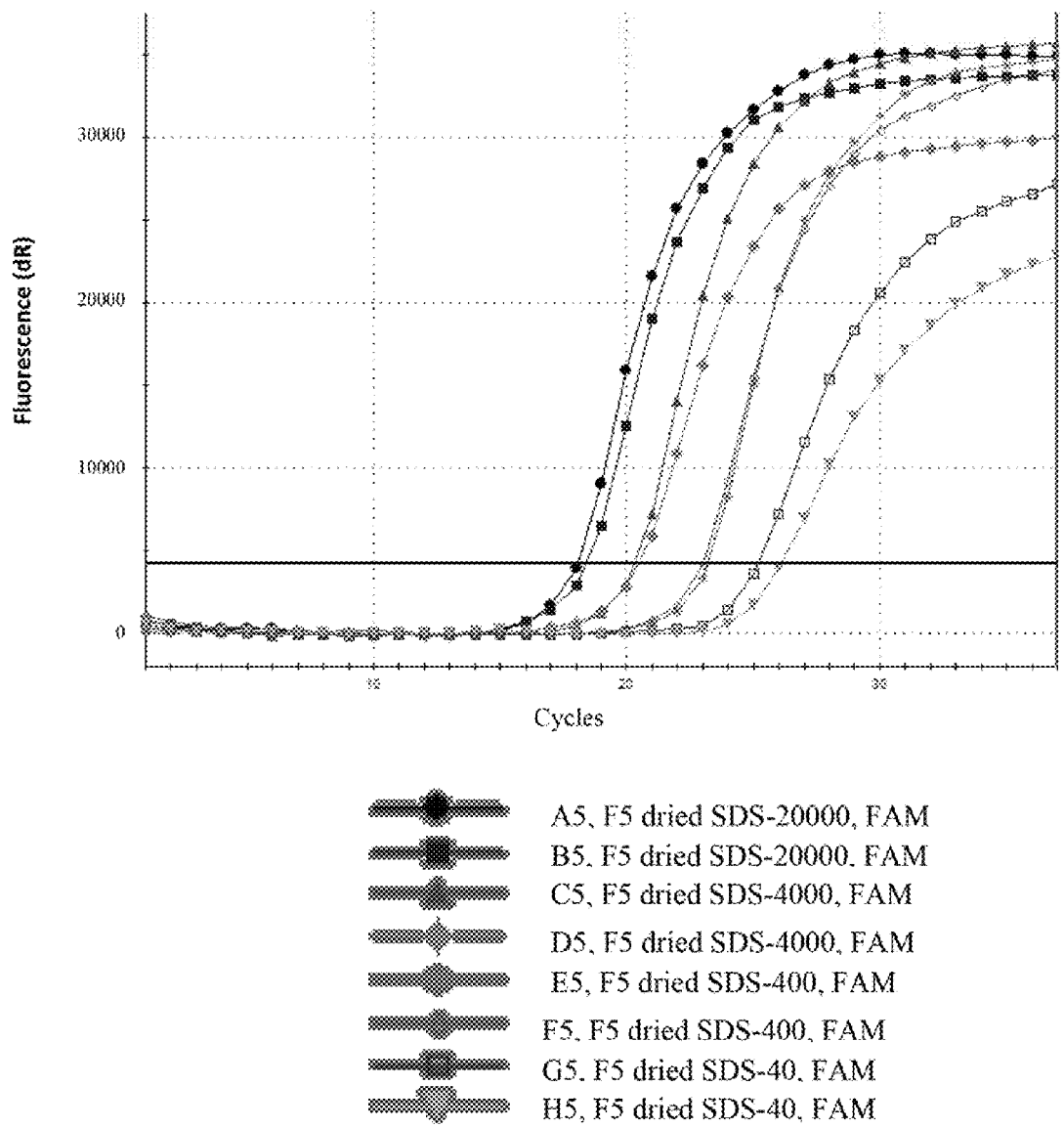
FIG. 18 shows blood samples containing HIV-1 (20,000-40 copies) lysed by adding to a filter membrane containing dried lysing reagent and tested for HIV-1 using real-time PCR.
Figure 19:
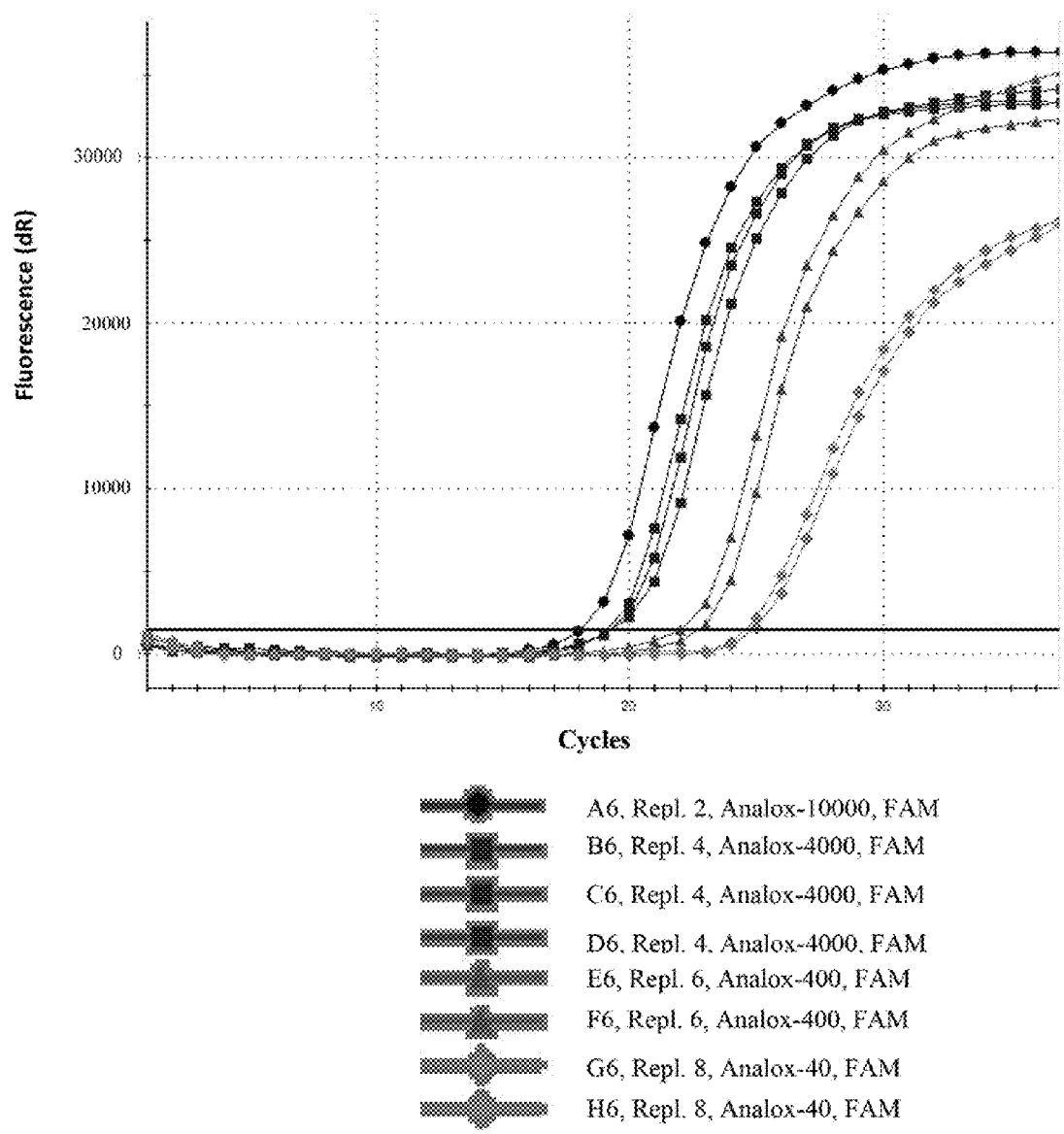
FIG. 19 shows blood samples containing HIV-1 (10,000-40 copies) were collected using an Analox lysing capillary. The sample gets lysed during collection and nucleic acid isolation is done by adding to a filter membrane and washing as described before.

Step 1 in which Blood Samples are Pre-Lysed can be Done in Various Ways:

1. In the method described above, 10 µl of lysing solution (10% Triton-X-1000R 0.5% SDS) was added to 100 µl blood in a microcentrifuge tube and finger-tapped a few times until the sample becomes translucent. The lysate was then added to the filter membrane.
2. In another method, 100 µl of lysing solution (1% Triton-X-100, 1% Trehalose OR 0.5% SDS) is lyophilized to obtain a pellet of lysing agent. For cell lysis, blood was added to this pellet which resuspends instantly and forms a translucent lysate on finger-tapping a few times. Washing was done as described above and real-time PCR was performed (FIG. 17)
3. In another method, lysing solution (1% Triton-X-100 or 0.5% SDS) was added to the filter membrane which was then dried. Blood was then added directly to the membrane impregnated with lysing material. This traped the genomic DNA and washing was done as described before with 10 mM NaOH followed by real-time PCR (FIG. 18).
4. In another method, capillaries containing dried lysing agents (Saponin) obtained from Analox Instruments USA Inc. were used to collect blood which were then lysed in the capillaries and added to the filter membrane followed by washing and real-time PCR (FIG. 19).

Devices Needed to Adapt Aforementioned Methods to Point-of-Care Testing

The above mentioned protocol simplifies the process of nucleic acid extraction and cell capture. It also makes the process rapid and inexpensive to perform in a laboratory. This method can also be used for point-of-care diagnostic testing. In order to adapt the method to point-of-care testing, the following embodiments can be used namely, 1) Sample collection/lysing device 2) Separation module 3) Wash dropper/container.

Sample Collection/Lysing Device

Figure 20:
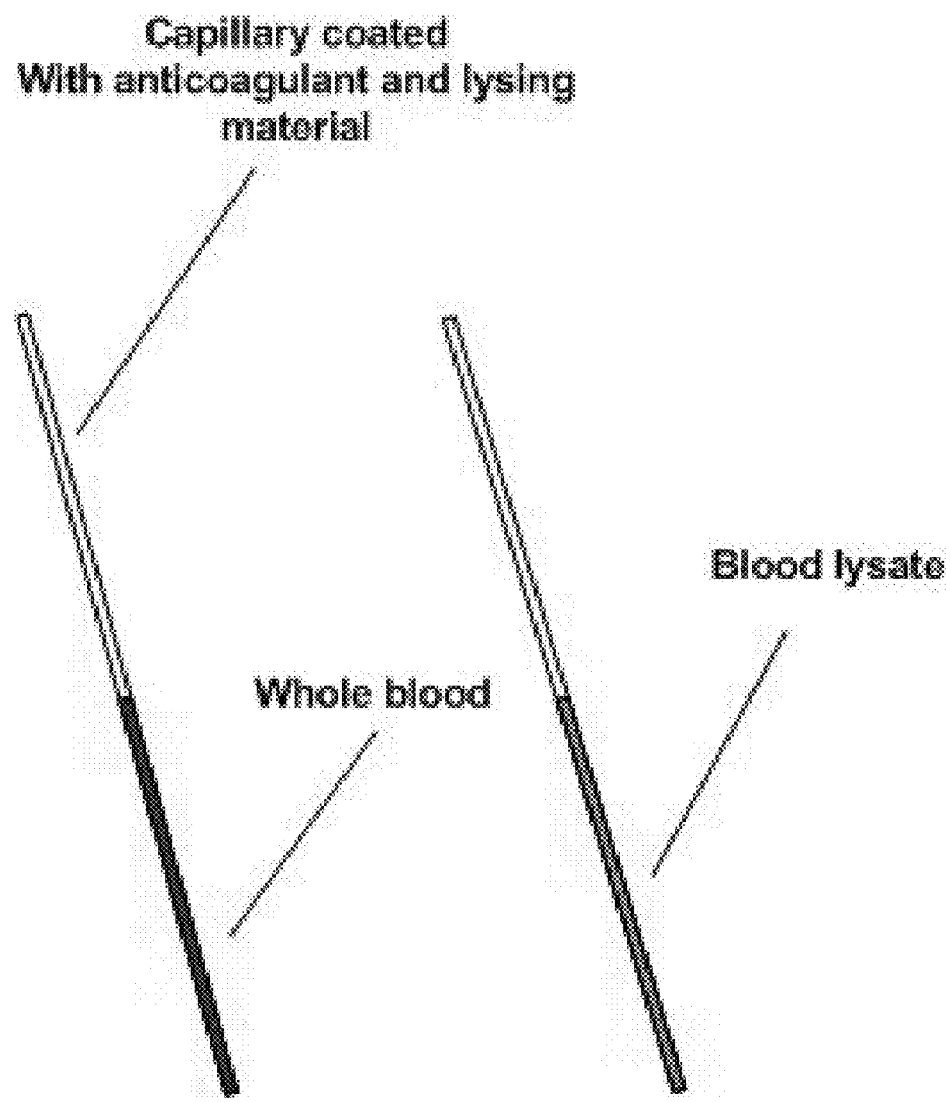
FIG. 20 shows capillary devices for blood collection.

This device is used for the first step of blood collection and/or lysing. Any of the following collection devices can be used for blood collection and/or pre-lysis. FIG. 20 describes a capillary device which is commonly used for blood collection. The device can be coated on the inside with lysing reagents and anticoagulants to prevent clotting and to lyse the blood as soon as it is collected.

Figure 21:
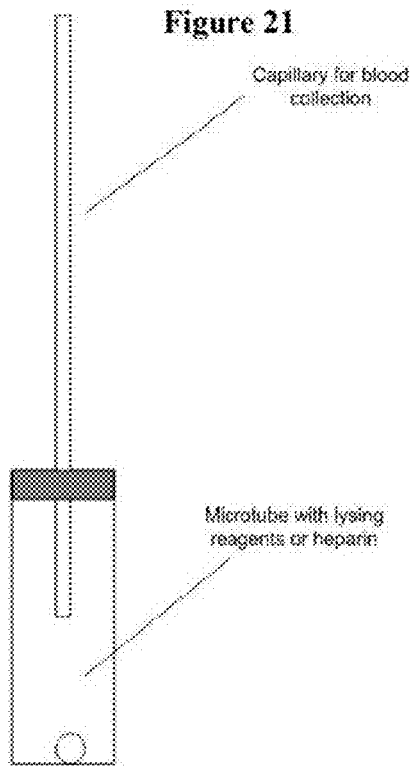
FIG. 21 shows a composite device consisting of capillary and microtube.

FIG. 21 shows a collection device also commonly used in the blood collection industry and is a composite of a capillary and microtube wherein the microtube contains dried lysing reagents and anti-coagulants.

Figure 22:
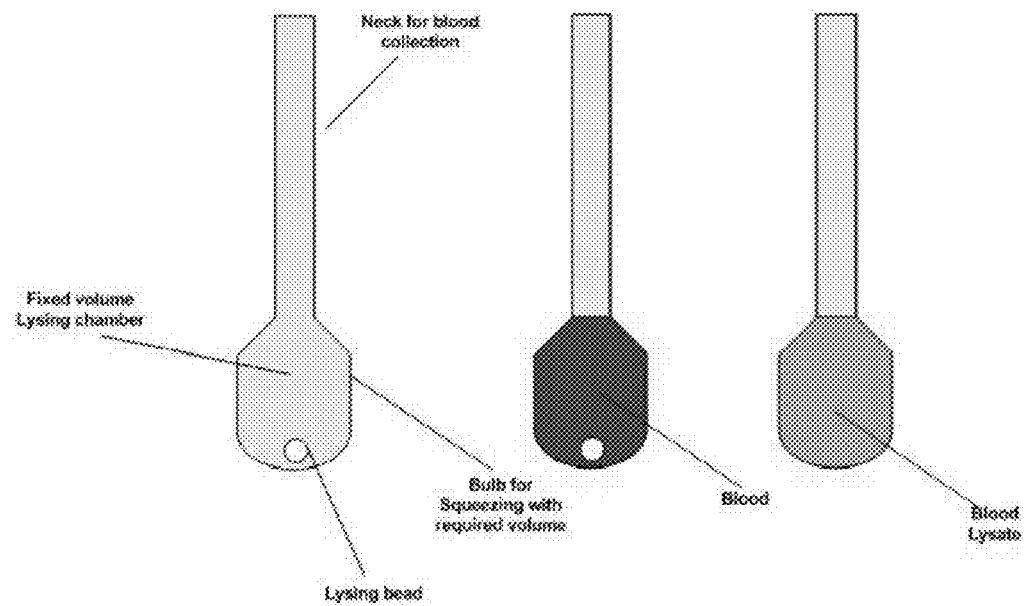
FIG. 22 shows usage of plastic transfer pipet like device for blood collection.

In addition to the above, a novel blood collection device very similar to a plastic transfer pipet can also be used as shown in FIG. 22. The following blood collection device can be made of plastic and has a bulb which can be used as a lysing chamber after blood collection. After pre-lysis, the bulb can be squeezed to inject the blood lysate onto a separation module. The bulb is coated with lysing material via freeze-drying or gel-encapsulation. Alternatively, a bead of lysing material can be dropped into the device. The bulb has the same volume as the required volume of blood.

When lysis of blood is not performed, collection devices need not be used for blood collection. The separation module can be held up to the body (e.g., an infant's heel or an adult's finger) to collect blood after puncture using a lancet.

Separation Module

Figure 23:
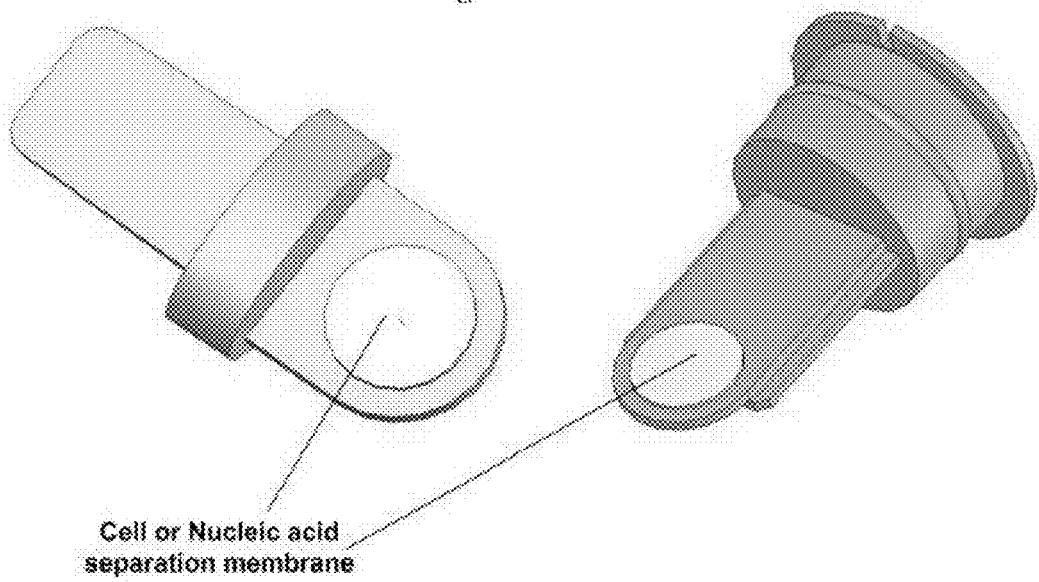
FIG. 23 shows a SIM with a separation membrane.
Figure 24:
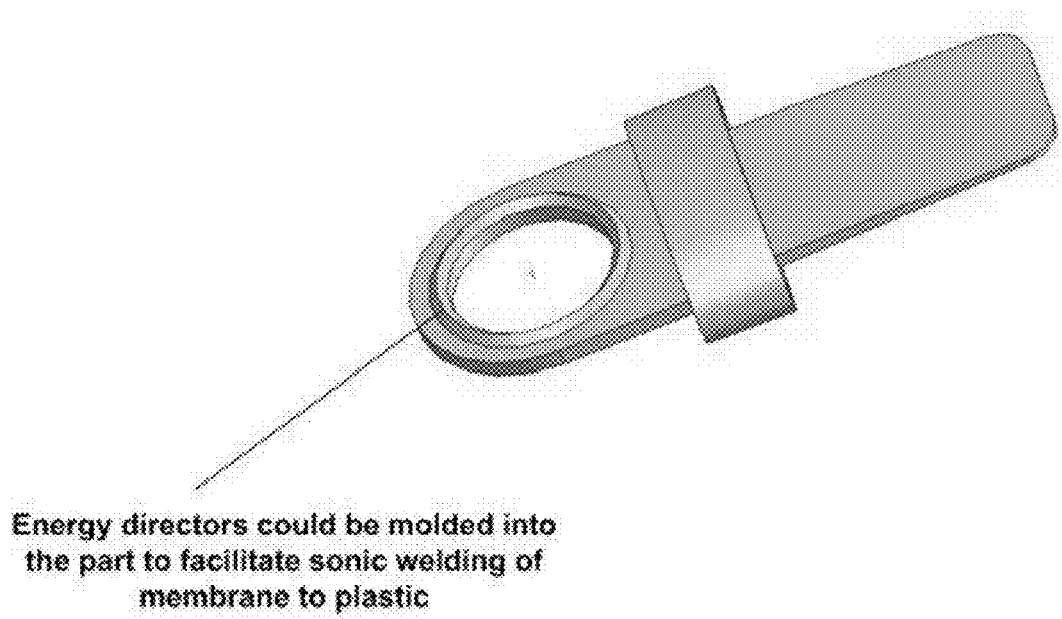
FIG. 24 shows that a SIM could possibly have energy directors for ultrasonic welding of membrane to plastic.

The separation module consists of a separation device and a sample SIM also referred to as the sample introduction module (SIM). FIG. 23 shows a SIM where the separation membrane is bonded to a plastic SIM that introduces the analyte of interest (cells or nucleic acids) into a reaction vessel. The separation membrane can be bonded to the plastic SIM via ultrasonic welding using energy directors (FIG. 24) or by laser welding or by adhesive bonding.

Figure 25:
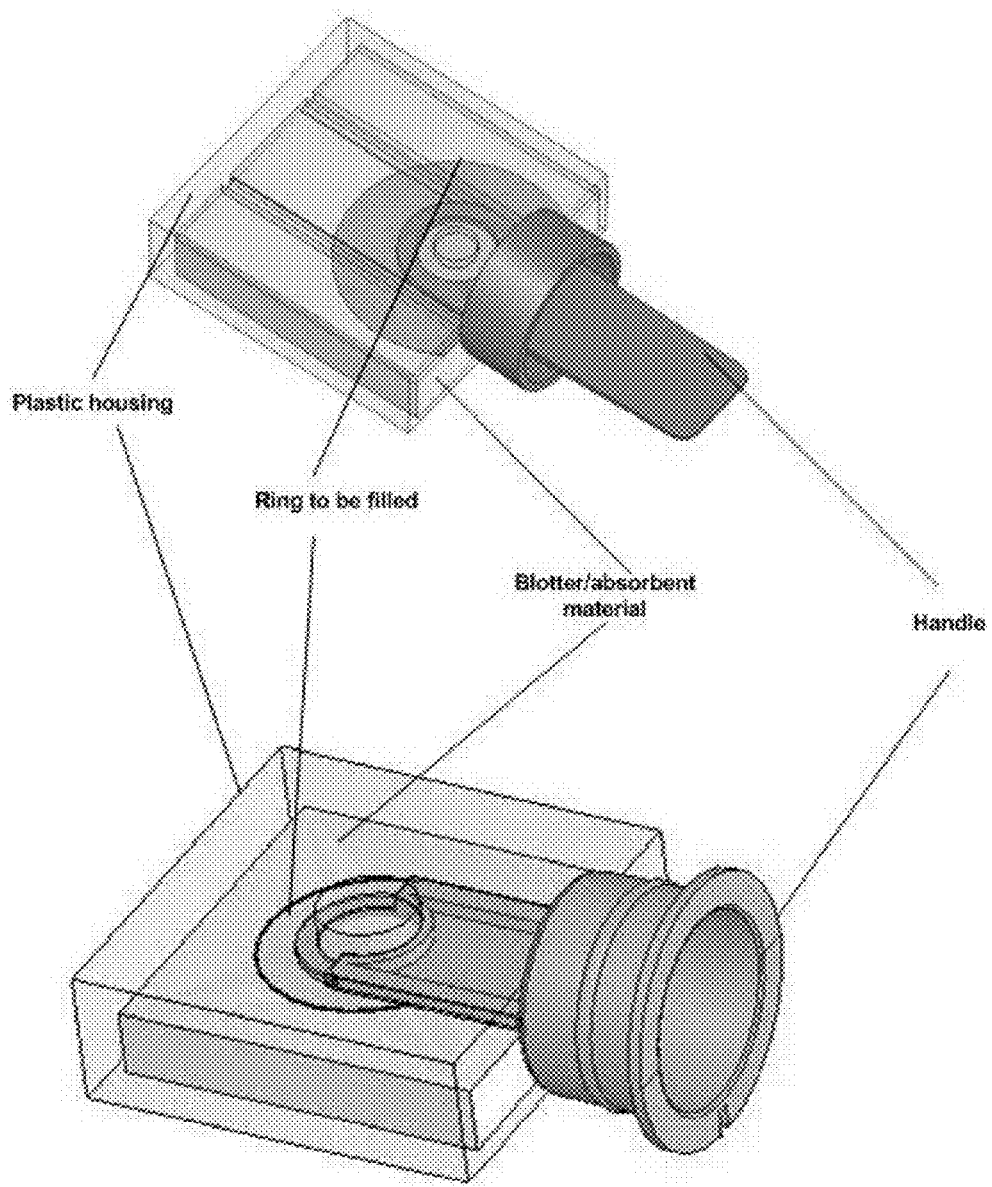
FIG. 25 shows a separation device with ring to aid in blood collection.
Figure 26:
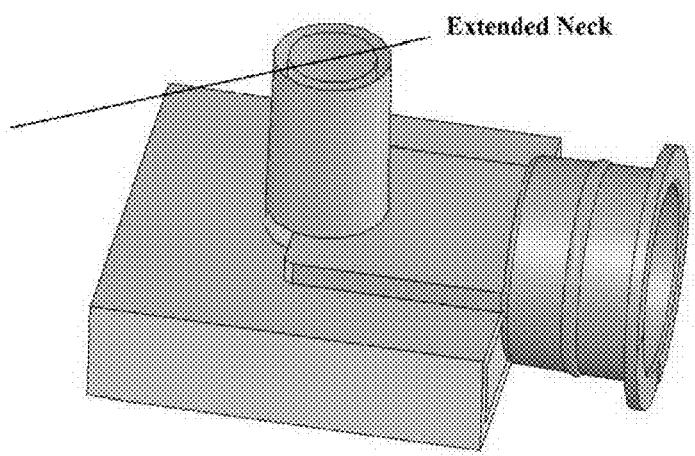
FIG. 26 shows a separation device with extended neck to aid in blood collection directly from the heel without the need for a collection device.
Figure 27:
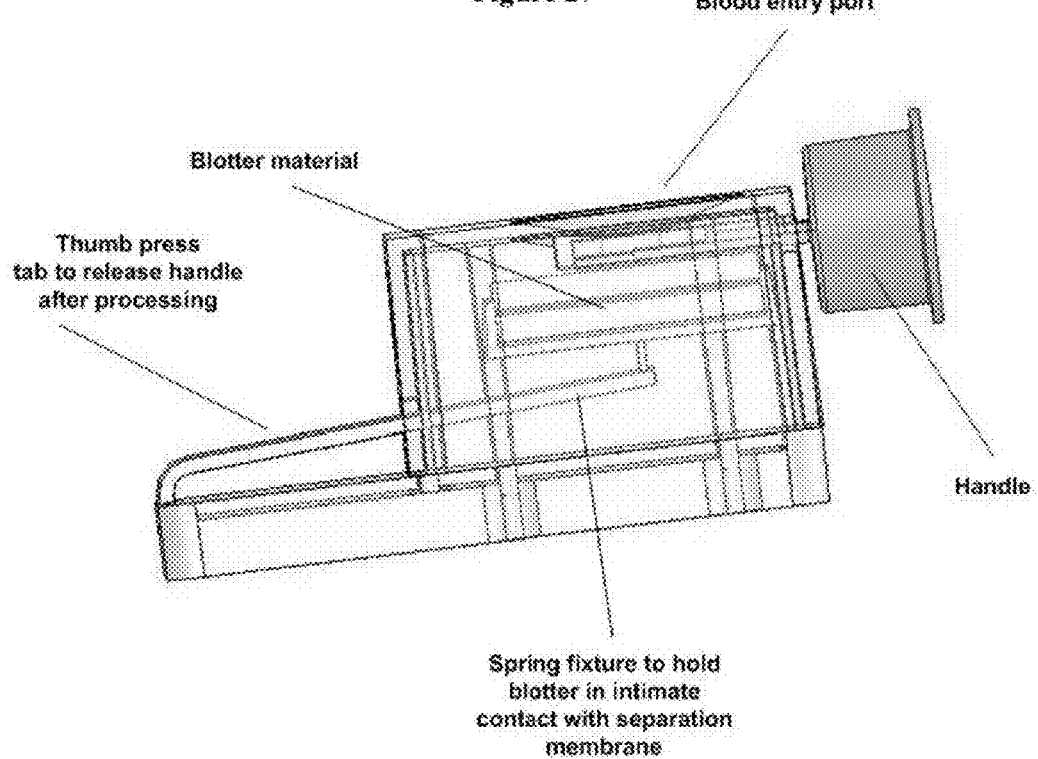
FIG. 27 shows a separation module with spring fixture for improved contact of blotter material with separation membrane.
Figure 28:
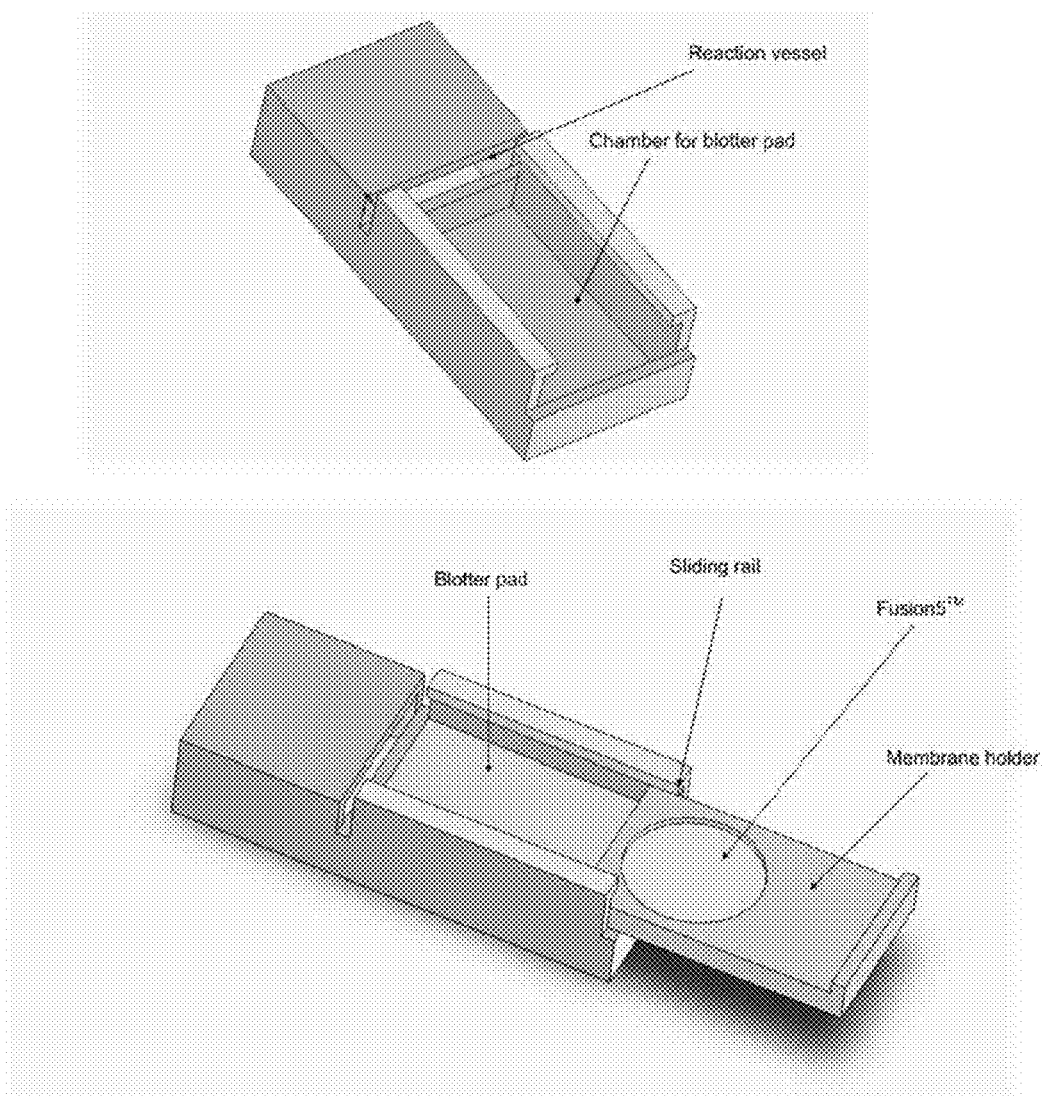
FIG. 28 shows a composite device of separation module and reaction vessel.

The aforementioned SIMs mate with a separation device that houses an absorbent material which could be a blotter pad. FIG. 25 shows a separation device that ensures intimate contact between the separation membrane and the blotter material so as to enable fast wicking. The plastic device can also have a visualization ring printed or molded on top as an indicator of blood volume collected when a blood collection device is not used. The top surface of the device could be polished so that the operator can visualize how much blood has been collected and ascertain if the ring has been filled.

Alternatively blood can be collected via one of the aforementioned collection devices with a fixed volume and added onto the separation device in which case printed/molded visualization rings are note needed. When lysis of blood is not performed, collection devices need not be used for blood collection. The separation module can be held up to the body (e.g., an infant's heel or an adult's finger) to collect blood after puncture using a lancet.

In another embodiment of the separation module, the module may have a spring fixture that improves contact between the blotter material and the separation membrane. The module also has a tab that can be pressed to release the SIM after sample processing. In yet another embodiment, the separation module can be a part of the reaction vessel. The composite device has a rail on which the SIM can slide and enter the reaction vessel after sample processing.

Wash Dropper/Container

This container stores the wash buffer and could be any of the following:
a) Plastic/glass dropper bottle
b) Squeeze bottles
c) Spout liquid pouches
d) Liquid blister packs
e) Liquid dispensers The above containers may be lined with aluminum foil to minimize evaporation.

All publications, patents, patent applications and sequences identified by accession numbers mentioned in the above specification are herein incorporated by reference in their entirety. Although the invention has been described in connection with specific embodiments, it should be understood that the invention as claimed should not be unduly limited to such specific embodiments. Modifications and variations of the described compositions and methods of the invention that do not significantly change the functional features of the compositions and methods described herein are intended to be within the scope of the following claims.

We claim:

1. A method of processing biological samples, comprising:
a) contacting with a blood sample at least one sample processing device comprising
  (i) a sample collection membrane with a pore size configured to retain nucleic acid and allow lysed red blood cells to flow through, and
  (ii) a blotter material in physical contact with said membrane; and
b) contacting said membrane with a buffer under conditions such that said buffer lyses red blood cells, removes debris, and leaves purified white blood cells or components thereof on said membrane.

2. The method of claim 1, wherein said nucleic acid is in white blood cell nuclei.

3. The method of claim 1, further comprising the step of lysing said white blood cells and said red blood cells prior to contacting said sample with said sample processing device.

4. The method of claim 1 wherein said physical contact permits horizontal lateral flow of fluid from said membrane to said blotter.

5. The method of claim 1, wherein said physical contact permits vertical flow of fluid from said membrane to said blotter.

6. The method of claim 1, further comprising the step of performing a nucleic acid detection reaction on said purified white blood cells.

7. The method of claim 6, wherein said nucleic acid detection reaction is an amplification reaction.

8. The method of claim 7, wherein said amplification reaction is selected from the group consisting of polymerase chain reaction, loop mediated isothermal amplification, ligase chain reaction, rolling circle replication, nucleic acid sequence based amplification and self-sustained sequence replication.

9. The method of claim 1, wherein said method purifies up to 200 µl of blood.

10. The method of claim 1, further comprising the step of detecting said amplified nucleic acid.

11. The method of claim 10, wherein said amplified nucleic acid is pathogen nucleic acid.

12. The method of claim 11, wherein said pathogen is a virus.

13. The method of claim 6, wherein nucleic acid is genomic DNA.

14. A biological sample processing kit, comprising:
a) at least one sample processing device comprising
  (i) a sample collection membrane with a pore size configured to retain nucleic acid and allow lysed red blood cells to flow through and
  (ii) a blotter material in physical contact with said membrane; and
b) a buffer configured to lyse red blood cells retained on said membrane.

15. The kit of claim 14, wherein said nucleic acid is in white blood cell nuclei.

16. The kit of claim 14, wherein said nucleic acid is in white blood cells.

17. The kit of claim 14, wherein said physical contact permits horizontal lateral flow of fluid from said membrane to said blotter.

18. The kit of claim 14, wherein said physical contact permits vertical flow of fluid from said membrane to said blotter.

19. The kit of claim 14, further comprising reagents for performing a nucleic acid detection reaction.

20. The kit of claim 19, wherein said nucleic acid detection reaction is an amplification reaction.

21. The kit of claim 20, wherein said amplification reaction is selected from the group consisting of polymerase chain reaction, loop mediated isothermal amplification, ligase chain reaction, rolling circle replication, nucleic acid sequence based amplification and self-sustained sequence replication.

22. The kit of claim 14, wherein said membrane holds up to 200 µl of blood.

23. The kit of claim 20, further comprising reagents for detecting said amplified nucleic acid.

24. The kit of claim 23, wherein said amplified nucleic acid is pathogen nucleic acid.

25. The kit of claim 24, wherein said pathogen is a virus.

26. The kit of claim 19, wherein nucleic acid is genomic DNA.

27. The kit of claim 14, further comprising reagents for lysing cells comprising said nucleic acid and lysing red blood cells.

* * * * *